US010246720B2

(12) United States Patent
Good et al.

(10) Patent No.: US 10,246,720 B2
(45) Date of Patent: Apr. 2, 2019

(54) PLANTS HAVING ENHANCED NITROGEN EFFICIENCY

(75) Inventors: Allen Good, Edmonton (CA); Yee Ying Lock, Edmonton (CA); Perrin H. Beatty, Edmonton (CA)

(73) Assignee: BAYER INTELLECTUAL PROPERTY GMBH, Monheim am Rhein (DE)

( * ) Notice: Subject to any disclaimer, the term of this patent is extended or adjusted under 35 U.S.C. 154(b) by 1316 days.

(21) Appl. No.: 14/343,813

(22) PCT Filed: Sep. 7, 2012

(86) PCT No.: PCT/CA2012/050622
§ 371 (c)(1),
(2), (4) Date: Jun. 25, 2014

(87) PCT Pub. No.: WO2013/033846
PCT Pub. Date: Mar. 14, 2013

(65) Prior Publication Data
US 2014/0380525 A1    Dec. 25, 2014

Related U.S. Application Data

(60) Provisional application No. 61/532,016, filed on Sep. 7, 2011.

(51) Int. Cl.
| | | |
|---|---|---|
| *C12N 15/29* | (2006.01) | |
| *C12N 15/82* | (2006.01) | |
| *C12N 9/10* | (2006.01) | |
| *C12N 9/02* | (2006.01) | |

(52) U.S. Cl.
CPC ....... *C12N 15/8261* (2013.01); *C12N 9/1096* (2013.01); *C12Y 206/01002* (2013.01); *C12N 9/0008* (2013.01); *C12Y 102/01027* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 7,390,937 B2 | 6/2008 | Good et al. | |
| 7,589,257 B2 | 9/2009 | Hershey et al. | |
| 7,982,093 B2 | 7/2011 | Good et al. | |
| 2007/0162995 A1* | 7/2007 | Good | C12N 9/1096 800/278 |
| 2009/0288224 A1 | 11/2009 | Good et al. | |
| 2014/0380525 A1* | 12/2014 | Good | C12N 9/0008 800/290 |

FOREIGN PATENT DOCUMENTS

| | | |
|---|---|---|
| WO | 01/55433 | 8/2001 |
| WO | 2007/076115 | 7/2007 |

OTHER PUBLICATIONS

Son et al. (1992, Plant Molecular Biology 20:705-713).*
Muench et al. (1994 Plant Molecular Biology 24:417-427).*
Orsel et al. (Journal of Experimental Botany, vol. 53, No. 370, 825-833, Apr. 2002).*
Oguchi et al. (Plant Cell Rep 2004, 22:848-858).*
Genbank accession AP005179, entered May 15, 2002.*
Baud et al. (Plant Physiol. Biochem. 40 (2002) 151-160).*
Extended European Search Report issued in corresponding European Patent Application No. EP12829500.3, dated Jan. 14, 2015.
International Search Report and Written Opinion issued in International Patent Application No. PCT/CA2012/050622 dated Dec. 3, 2012 (9 pages).
Office Action issued in Australian Patent Application No. 2012307006 dated Jan. 6, 2017 (3 pages).
Office Action issued in European Patent Application No. 12829500.3 dated Jul. 5, 2016 (5 pages).
Office Action issued in Ukranian Patent Application No. a 2014 03599 dated Sep. 7, 2012 (14 pages).
Altschul, S. et al., "Basic Local Alignment Search Tool," J. Mol. Biol. (1990), vol. 215, pp. 403-410.
Beatty, P. et al., "Transcriptome Analysis of Nitrogen-Efficient Rice Over-expressing Alanine Aminotransferase," Plant Biotechnology Journal (2009), vol. 7, pp. 562-576.
Burton, R. et al., "Over-expression of Specific HvCsIF Cellulose Synthase-like Genes in Transgenic Barley Increases the Levels of Cell Wall (1,3;1,4)-B-D-glucans and Alters Their Fine Structure," Plant Biotechnology Journal (2011), vol. 9, pp. 117-135.
Freeman et al., "Temporal and Spatial Control of Transgene Expression Using a Heat-inducible Promoter in Transgenic Wheat," Plant Biotechnology Journal (2011), vol. 9, pp. 788-796.
Furtado, A. et al., "Comparison of Promoters in Transgenic Rice," Plant Biotechnology Journal (2008), vol. 6, pp. 679-693.
Gao, C. et al., "Evolutionary and Expression Study of the Aldehyde Dehydrogenase (ALDH) Gene Superfamily in Rice (*Oryza sativa*)," Gene (2009), vol. 431, pp. 86-94.
Good, A. et al., "Engineering Nitrogen Use Efficiency with Alanine Aminotransferase," Canadian Journal of Botany (2007), vol. 85, pp. 252-262.
Good, A. et al., "Biotechnological Approaches to Improving Nitrogen Use Efficiency in Plants: Alanine Aminotransferase as a Case Study," The Molecular and Physiological Basis of Nutrient Use Efficiency in Crops (2011) (1st Ed., John Wiley & Sons, Inc.).
Kasuga, M. et al., "Improving Plant Drought, Salt, and Freezing Tolerance by Gene Transfer of a Single Stress-Inducible Transcription Factor," Nature Biotechnology (1999), vol. 17, pp. 287-291.

(Continued)

*Primary Examiner* — Mykola V. Kovalenko
*Assistant Examiner* — Charles Logsdon
(74) *Attorney, Agent, or Firm* — Arent Fox LLP

(57) ABSTRACT

A transgenic plant comprising a polynucleotide encoding a nitrogen utilization protein operably linked to a PBpr1 promoter is provided. The transgenic plant exhibits increased nitrogen use efficiency, increased biomass and/or increased seed yield. Seeds from such transgenic plants, genetic constructs to prepare such plants, methods of generating and growing transgenic plants are also provided.

13 Claims, 18 Drawing Sheets

Specification includes a Sequence Listing.

(56) References Cited

OTHER PUBLICATIONS

Ma, Q. et al., "Expression of Isopentenyl Transferase Gene (ipt) in Leaf and Stem Delayed Leaf Senescence Without Affecting Root Growth," Plant Cell Rep. (2009), vol. 28, pp. 1759-1765.
Miyashita, Y. et al., "Alanine Aminotransferase Catalyses the Breakdown of Alanine After Hypoxia in Arabidopsis Thaliana," The Plant Journal (2007), vol. 49, pp. 1108-1121.
Muench, D. et al., "Hypoxically Inducible Barley Alanine Aminotransferase: cDNA Cloning and Expression Analysis," Plant Molecular Biology (1994), vol. 24. pp. 417-427.
Oguchi, K. et al., "Methylmalonate-semialdehyde Dehydrogenase in Induced in Auxin-stimulated and Zinc-Stimulated Root Formation in Rice," Plant Cell Reports (2004), vol. 22, pp. 848-858.
Park, et al., "A new Resistance Gene to Powdery Mildew Identified in Solanum Neorossii has been Localized on the Short Arm of Potato Crhomosome 6," Euphytica (2009), vol. 166, pp. 331-339.
Pino, M. et al., "Use of a Stress Inducible Promoter to Drive Ectopic AtCBF Expression Improves Potato Freezing Tolerance While Minimizing Negative Effects on Tuber Yield," Plant Biotechnology Journal (2007), vol. 5, pp. 591-604.
Qu, L. et al., "Evaluation of Tissue Specificity and Expression Strength of Rice Seed Component Gene Promoters in Transgenic Rice," Plant Biotechnology Journal (2004), vol. 2, pp. 113-125.
Shelton, A. et al., "Economic, Ecological, Food Safety, and Social Consequences of the Deployment of BT Transgenic Plants," Annu. Rev. Entomol. (2002), vol. 47, pp. 845-881.
Shrawat, A. et al., "Genetic Engineering of Improved Nitrogen Use Efficiency in Rice by the Tissue-Specific Expression of Alanine Aminotransferase," Plant Biotechnology Journal (2008), vol. 6, pp. 722-732.
Shrawat, A. et al., "Agrobacterium tumefaciens-Medicated Genetic Transformation of Cereals Using Immature Embryos," Methods in Molecular Biology (2011), vol. 710, pp. 355-372.
Sweetlove, L. et al., "The Impact of Oxidative Stress on Arabidopsis Mitochondria," The Plant Journal (2002), vol. 32, pp. 891-904.
Tanaka, N. et al., "Proteome Approach to Characterize the Methylmalonate-Semialdehyde Dehydrogenase That is Regulated by Gibberellin," Journal of Proteome Research (2005), vol. 4, pp. 1575-1582.
Weber, D., "Colorado Beetle: Pest on the Move," Pesticide Outlook (2003), vol. 14, pp. 256-259.
Wu, C. et al., "Promoters of Rice Seed Storage Protein Genes Direct Endosperm-Specific Gene Expression in Transgenic Rice," Plant Cell Physiology (1998), vol. 39, No. 8, pp. 885-889.
Xue et al., "Overexpression of TaNAC69 Leads to Enhanced Transcript Levels of Stress Up-Regulated Genes and Dehydration Tolerance in Bread Wheat," Molecular Plant (2011), vol. 4, No. 4, pp. 697-712.
Smith, T. et al., "Identification of Common Molecular Subsequences," J. Mol. Biol. (1981), vol. 147, pp. 195-197.
GenBank Accession No. AF045770.1, Oryza sativa methylmalonate semi-aldehyde dehydrogenase.(MMSDH1) mRNA, complete cds, last updated date Feb. 19, 1998 (2 pages).
GenBank Accession No. AK121280.1, "Oryza sativa Japonica Group cDNA clone:J023108H13, full insert sequence," last updated date Dec. 4, 2008 (4 pages).
Notice of Acceptance issued in Australian Patent Application No. 2012307006 dated Jul. 24, 2017 (3 pages).
Office Action issued in European Patent Application No. 12829500.3 dated Mar. 28, 2017 (6 pages).
Office Action issued in Ukrainian Patent Application No. a 2014 03599, dated Aug. 16, 2017 (10 pages).
Office Action issued in Canadian Patent Application No. 2,847,715, dated May 8, 2018 (5 pages total).

\* cited by examiner

A.
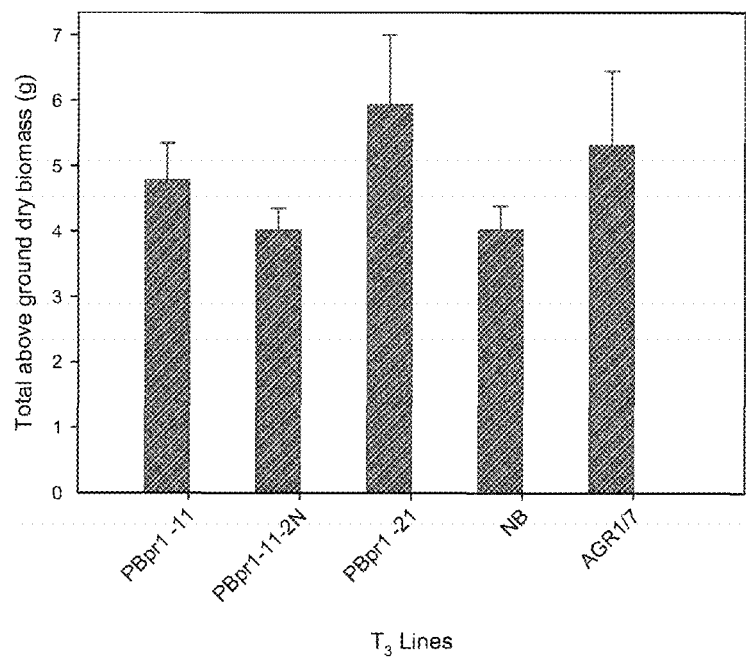
B.
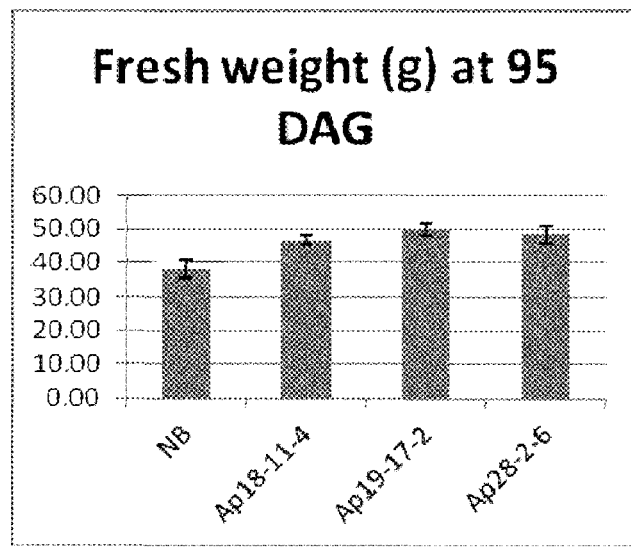
FIG. 5

```
      EcoRI
  1 GAATTCGAA AGTTCCGTC CAAATCGCAC CTTTTAACCG TTTGAAAAAC ATACAAACGA AAAATAATCT ATATCTTAAT CAGGAAGAAA GAGTACGAAA
    CTTAAGCTT TCAAGGCAG GTTTAGCGTG GAAAATTGGC AAACTTTTTG TATGTTTGCT TTTTATTAGA TATAGAATTA GTCCTTCTTT CTCATGCTTT

101 TGGTGAACCG TCGAAACTAT TCATATACGT CGTCTGTCTC ATGAAAAAAA AAATCAATCC AGAAGGATAC GAGACACTTT TACTTCAACA AATATAGACA
    ACCACTTGGC AGCTTTGATA AGTATATGCA GCAGACAGAG TACTTTTTTT TTTAGTTAGG TCTTCCTATG CTCTGTGAAA ATGAAGTTGT TTATATCTGT

201 TGAGCTTATT CTACTAGGTT TGGTTGTTTA ATAAGACGAA AGAAATACAT TGGTTAGTTT TTCATTAAAA AATAATCGTT TGACTGACAT AAACCTAGGA
    ACTCGAATAA GATGATCCAA ACCAACAAAT TATTCTGCTT TCTTTATGTA ACCAATCAA AAGTAATTTT TTATTAGCAA ACTGACTGTA TTTGGATCCT

301 AATACTGGAT TAAGATAGAT CAGTAGGATT AAGAATCCACT GATGTAATTT CCCACTGATT TGGTGGCTGA CATGTGGACC TGAGAGTTGT GTGGGCTCAC
    TTATGACCTA ATTCTATCTA GTCATCCTAA TTCTAGGTGA CTACATTAAA GGGTGACTAA ACCACCGACT GTACACCTGG ACTCTCAACA CACCCGAGTG

401 ATGTCAAATC ACGGTGAACA GTACGTCACG ATATGTTAGA GGTTCCTCTT CCGGAGATAC TTATACGAAT TTTGCGGAAA CCTGCAAACT TTGATGGACG
    TACAGTTTAG TGCCACTTGT CATGCAGTGC TATACAATCT CCAAGGAGAA GGCCTCTATG AATATGCTTA AAACGCCTTT GGACGTTTGA AACTACCTGC

501 ATTGAGGCGA GTTTAGTTCT AAATTTTTTC TTCAAACTTC TAACTTTTTC ATCACATCGT TCGAATTTCA CAATGTTGAC GTGAACTAAA
    TAACTCCGCT CAAATCAAGA TTTAAAAAAG AAGTTTGAAG ATTGAAAAAG TAGTTAGCA AGCTTAAAGT TAGTTTGAAG GTTACAACTG CACTTGATTT

601 CACACCTATG AGATATGAGA AGCGGGTTGA CACTTGACAA GTCCTGACAT GCTGTGTTGG CGTGGGCCCC ACCTGCCACG TCAGGTCCAG CTCCGGGTGG
    GTGTGGATAC TCTATACTCT TCGCCCAACT GTGAACTGTT CAGGACTGTA CGACACAACC GCACCCGGGG TGGACGGTGC AGTCCAGGTC GAGGCCCACC

SacI
701 TTGGGTTTGG TGCTTTCCGA TAGGCACGAG CTC ATGGCTG CCACC
    AACCCAAACC ACGAAAGGCT ATCCGTGCTC GAG TACCGAC GGTGG
```

FIG. 13

|  | 28 DAG | | | | | 40 DAG | | | | |
| --- | --- | --- | --- | --- | --- | --- | --- | --- | --- | --- |
| Amino acids | NB | AGR 1/7 | PBpr1-11 | PBpr1-12 | PBpr1-21 | NB | AGR 1/7 | PBpr1-11 | PBpr1-12 | PBpr1-21 |
| Glu | 5313.8 | 4344.2 | 4321.1 | 4421.3 | 4426.4 | 4322.8 | 5299.0 | 5771.8 | 5042.7 | 5018.9 |
| Ala | 3613.0 | 3143.7 | 3478.5 | 4549.0 | 3578.7 | 3442.4 | 4460.8 | 3801.1 | 4232.9 | 3692.7 |
| Asp | 1578.7 | 1103.0 | 1258.7 | 1155.1 | 1034.8 | 1200.4 | 1264.9 | 1554.6 | 1168.4 | 1228.7 |
| Ser | 1568.5 | 930.4 | 1566.1 | 1006.9 | 590.8 | 982.8 | 583.2 | 1392.0 | 635.4 | 492.0 |
| Thr | 664.0 | 489.2 | 736.5 | 545.0 | 438.4 | 453.7 | 535.2 | 686.9 | 482.7 | 457.2 |
| Asn | 644.2 | 338.9 | 1129.6 | 620.8 | 389.2 | 79.5 | 80.1 | 157.3 | 56.3 | 58.4 |
| Gln | 597.5 | 1342.8 | 2805.3 | 1180.6 | 952.2 | 199.6 | 429.1 | 629.7 | 253.1 | 309.1 |
| Gly | 304.9 | 276.7 | 426.3 | 530.2 | 354.8 | 197.9 | 276.2 | 330.6 | 315.2 | 254.7 |
| GABA | 293.4 | 173.5 | 394.8 | 258.9 | 280.3 | 229.3 | 201.2 | 196.9 | 163.2 | 144.7 |
| Val | 204.0 | 246.5 | 414.6 | 279.6 | 239.7 | 198.5 | 213.4 | 246.6 | 231.0 | 225.8 |
| His | 167.6 | 189.3 | 202.2 | 164.8 | 133.1 | 181.4 | 156.2 | 173.0 | 182.2 | 140.6 |
| Hyp | 166.2 | 92.9 | 144.9 | 140.6 | 108.3 | 152.4 | 134.3 | 152.9 | 126.1 | 107.3 |
| Pro | 113.4 | 90.0 | 107.8 | 86.9 | 99.1 | 83.0 | 65.8 | 114.0 | 86.4 | 74.7 |
| Lys | 56.2 | 56.0 | 75.8 | 70.2 | 48.5 | 52.5 | 42.6 | 63.1 | 50.3 | 45.4 |
| Leu | 39.0 | 58.7 | 57.6 | 53.6 | 61.8 | 37.6 | 49.0 | 53.1 | 47.5 | 53.3 |
| Tyr | 32.3 | 50.4 | 86.7 | 34.4 | 49.2 | nd | nd | 109.9 | nd | nd |
| Arg | nd | nd | 294.2 | 81.1 | nd | 41.5 | 41.5 | nd | 44.1 | 52.3 |
| Cys | nd | nd | nd | nd | nd | nd | nd | nd | nd | nd |
| Met | nd | nd | 24.8 | nd | nd | nd | nd | nd | 13.9 | nd |
| Trp | nd | 16.4 | 58.0 | 16.7 | nd | nd | nd | 24.3 | nd | nd |
| Phe | nd | nd | 53.2 | 17.2 | 14.3 | nd | 19.1 | 42.5 | 38.3 | 35.4 |
| Ile | nd | 27.1 | 124.9 | 38.9 | 35.5 | 42.4 | nd | 55.3 | 33.1 | 41.2 |
| TOTAL | 15356.8 | 12969.6 | 17761.6 | 15251.8 | 12835.0 | 11897.7 | 13851.7 | 15555.5 | 13202.8 | 12432.4 |
|  | 52 DAG | | | | | 95 DAG | | | | |
| Amino acids | NB | AGR 1/7 | PBpr1-11 | PBpr1-12 | PBpr1-21 | NB | AGR 1/7 | PBpr1-11 | PBpr1-12 | PBpr1-21 |
| Glu | 5210.8 | 5186.8 | 4880.6 | 5340.4 | 5340.4 | 4393.2 | 5500.2 | 4431.5 | 4512.8 | 3750.9 |
| Ala | 3080.7 | 3011.1 | 3536.2 | 2836.1 | 2836.1 | 2388.6 | 1832.1 | 2142.7 | 2721.5 | 1801.4 |
| Asp | 1392.8 | 1423.2 | 1255.4 | 1673.0 | 1673.0 | 1023.3 | 1667.9 | 1431.4 | 1266.8 | 1129.9 |
| Ser | 801.9 | 1199.7 | 1018.8 | 971.0 | 971.0 | 622.8 | 791.5 | 533.6 | 512.5 | 520.8 |
| Thr | 414.3 | 524.8 | 491.9 | 454.0 | 454.0 | 252.7 | 347.8 | 261.3 | 280.4 | 185.1 |
| Asn | 169.1 | 254.6 | 139.0 | 165.3 | 165.3 | 296.5 | 161.9 | 39.1 | 103.3 | 25.9 |
| Gln | 428.1 | 412.0 | 240.6 | 369.6 | 369.6 | 405.1 | 282.3 | 202.4 | 216.0 | 261.9 |
| Gly | 371.0 | 397.2 | 377.2 | 378.4 | 378.4 | 351.3 | 333.2 | 374.1 | 490.4 | 327.8 |
| GABA | 212.9 | 198.3 | 148.3 | 116.8 | 116.8 | 197.8 | 111.2 | 139.6 | 128.4 | 122.6 |
| Val | 289.0 | 247.6 | 272.1 | 224.4 | 224.4 | 396.4 | 367.8 | 253.2 | 226.0 | 226.7 |
| His | 333.7 | 307.3 | 304.7 | 291.4 | 291.4 | 430.3 | 451.4 | 377.8 | 386.2 | 425.3 |
| Hyp | 111.1 | 152.4 | 115.6 | 97.9 | 97.9 | 122.8 | 93.5 | 85.5 | 132.5 | 52.8 |
| Pro | nd | 45.9 | 57.2 | 45.8 | 45.8 | 237.1 | 128.7 | 114.7 | 52.6 | 54.4 |
| Lys | nd | nd | nd | nd | nd | 220.8 | nd | nd | nd | nd |
| Leu | nd | nd | 24.1 | nd | nd | 76.8 | 112.9 | 29.0 | nd | nd |
| Tyr | nd | nd | nd | nd | nd | nd | nd | nd | nd | nd |
| Arg | nd | nd | nd | nd | nd | nd | nd | nd | nd | nd |
| Cys | nd | nd | nd | nd | nd | nd | nd | nd | nd | nd |
| Met | nd | nd | nd | nd | nd | nd | nd | nd | nd | nd |
| Trp | nd | nd | nd | nd | nd | nd | nd | nd | nd | nd |
| Phe | nd | 33.1 | 31.9 | 41.3 | 41.3 | 103.4 | 120.7 | 80.8 | 61.5 | 58.0 |
| Ile | 40.3 | nd | 32.1 | 31.7 | 31.7 | 85.7 | 137.2 | 27.1 | nd | nd |
| TOTAL | 12855.7 | 13393.9 | 12925.8 | 13037.2 | 13037.2 | 11604.4 | 12440.2 | 10523.9 | 11091.0 | 8943.5 |

FIG. 15

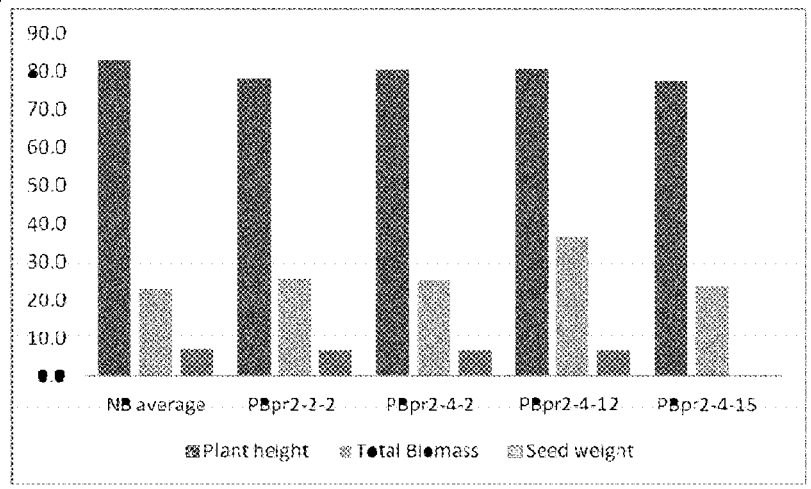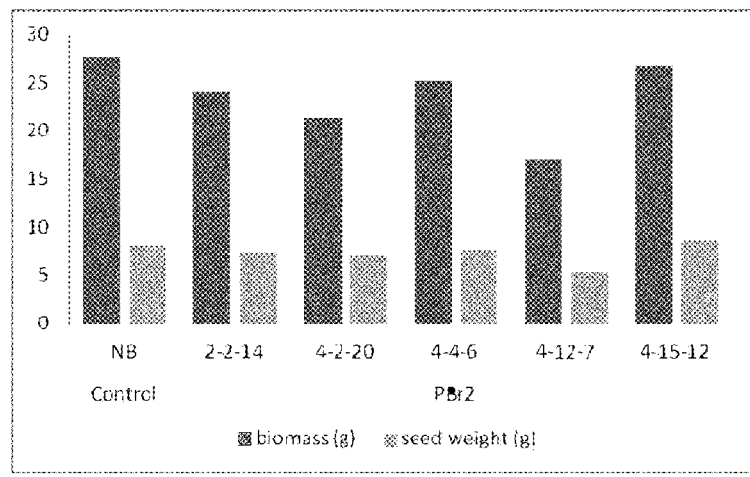
FIG. 16

```
                        1                                                 50
   O. sativa      (1)   AGGAAGTG  TT  GC  G  G   T   A C T  A T CG AA  G C
PBPr1 promoter   (1)   --------------------------------------------------
PBPr2 promoter   (1)   ------GA  CA  TA  T  T  A  T A C T A TA TC   G
Consensus        (1)         ATT  TA GTA CT TGT TGT G G A T G   T    AGT
                       51                                               100
   O. sativa     (51)   CT  CA TT  GC  TA C C C  C A- A  TTT C   TCTC C C
PBPr1 promoter   (1)   --------------------------------------------------
PBPr2 promoter  (45)   AG  A  AC  TA  GT G  T G G  TG  T  GAG T   GGAT T G
Consensus       (51)       TT AA  TT  TA T T A T GA AG TT   T TTA    T A
                       101                                              150
   O. sativa    (100)   C  AT T CTC C CAA  TTAC  TGTATT TCT G  ---  G   CA
PBPr1 promoter   (1)   --------------------------------------------------
PBPr2 promoter  (95)    G GG A TAT A  TTC  GGTA  ATAGGA GAG A  TAT A  GG
Consensus      (101)   T G  T T    A T    AT     AG      T   T TA   A TTA  G
                       151                                              200
   O. sativa    (147)   TG  AT   A AC  A  C G AACT TTG  AG   CA CTG  AT
PBPr1 promoter   (1)   ---GA  T C  A AG T   C  C - AAA T  CACC   T A CC-----  T
PBPr2 promoter (145)   AT  A T  CA TAT   A  GA  AT   A  T CA  ACAA  T
Consensus      (151)        TAAATTATGAAA TTTCAGT TCA ATCG TA TTTAAAC   TA GTT
                       201                                              250
   O. sativa    (197)     G  TCTTCA  A  TA  TTT  AAT  GT  TGGATTTG     TT
PBPr1 promoter  (43)    GA    ----A  ATACA  CG A AATAA T  --------A   TAA
PBPr2 promoter (195)    TTTT ----AGA  GATGGA  CAA    GA--------- ATA GC C
Consensus      (201)   TT AAA    ACATG AAA  ATAAATTTCTAT        GTCTT TT
                       251                                              300
   O. sativa    (247)   CTT   T TG  AATT  AT  TC TTA G   TTT C  AAG- GCT
PBPr1 promoter  (81)   CA   A  A  A  G A    GA CG C AA   T   A   CG
PBPr2 promoter (233)    C CT  GGT TCCA  A  C  CACGC ATATC   A  ACA AT  AA
Consensus      (251)   C GGAGGA AG GTAC ATATGGT   AC  T GTGACTATTCATATAC T
                       301                                              350
   O. sativa    (296)   TT G T   T  T  TCT T GGA  T T  TA AA   TAAA A TCT
PBPr1 promoter (131)        CTG  C  AT GA   AAA AAA  CAA C---  AGAAG TA   A  T
PBPr2 promoter (283)                CT TCG TCTC T G GTA A A ACCGTC T A C
Consensus      (301)   CGTCC TCTTATGA AA   A C T T T AACACAA GAT CGAGACACG
                       351                                              400
   O. sativa    (346)    G GA ----A   T AT A A  CTTTCG AAGA GTA   A ACT
PBPr1 promoter (179)    T AC TCAA CA   AT AGAC  G    AT- TA C- I    G T
PBPr2 promoter (333)    --------AC T CA          A   GCC   TC  GTCAG   G
Consensus      (351)   T T   T    ACGAATATAGA AT AGCTTA  TCT C TAGGTTTGC TG
                       401                                              450
   O. sativa    (393)     TT AA  AA  TT TCA GACAAAA  T  TGG  G  AGGTAG
PBPr1 promoter (227)   TT AA  GAC A  A    CAT G- AA T   T  AAAA ---
PBPr2 promoter (375)    CA   A  A AATAC   C  CA   TC  AA CCTC  A A AAA CTC
Consensus      (401)   A  ACTAATAAGAAAGTAATACAATG  TTAGTTTTCAATAAAAAA
                       451                                              500
   O. sativa    (443)   T AT G GAA  AG  ATG  GC  TT  AT TT  AT T  A TGCT AT G
PBPr1 promoter (273)   --TAA TC T  GAC  AC-  T  AC    A   A  CT  GA     TAAG T
PBPr2 promoter (425)   C A  TAA   AT  AA  G AT  G CAA A A    A TC AAA---TAG CC
Consensus      (451)    TAAA G TTAA TGAA ATAAG CTAGGAATTA TGCAT    TA TA
                       501                                              550
   O. sativa    (493)   C AC A  AACTAAT C ATAA T AA TGTT T TA ACGT CGCTTAA-T
PBPr1 promoter (317)    GATCAG A  --AT- AA  TC----C C G TG A T --TGC A -T
PBPr2 promoter (472)     AACA  AG--AT-AA A G A G GC AAACT CCA A TGG CA
Consensus      (501)   AAA CAATAGG  AT TAAGAG A  A CA T AT TAA TG TC CAC T
                       551                                              600
   O. sativa    (542)   A   AAAA  C AA   CA TG TAA A AA A CGAT GAA G-- AA G T A
```

FIG. 17

FIG. 17 (con.)

PLANTS HAVING ENHANCED NITROGEN EFFICIENCY

CROSS-REFERENCE TO RELATED APPLICATIONS

This application is the U.S. National Phase of International Patent Application No. PCT/CA2012/050622, filed Sep. 7, 2012, which claims benefit of U.S. Provisional Application No. 61/532,016, filed Sep. 7, 2011, the contents of each are hereby incorporated by reference in their entireties.

FIELD OF INVENTION

The present invention relates to monocot plants having enhanced yield and/or nitrogen utilization efficiency (NUE), to methods for enhancing yield and NUE in monocot plants, and to methods of increasing biomass and seed yield in monocot plants, for example, when grown under nitrogen limiting conditions.

BACKGROUND OF THE INVENTION

The productivity of plants is limited by the three primary nutrients: nitrogen, phosphorous and potassium, in most natural and agricultural ecosystems. Generally nitrogen is the most important of the three limiting nutrients and the major component in fertilizers. Since nitrogen is usually the rate-limiting element in plant growth, most field crops have a fundamental dependence on inorganic nitrogenous fertilizer. The nitrogen source in fertilizer is usually ammonium nitrate, potassium nitrate, or urea.

Increased nitrogen use efficiency by plants has a number of beneficial effects, for example, increased growth and yield when compared to conventional plants grown in nitrogen poor soils, and reduced requirement for the addition of nitrogenous fertilizers to crops. Fertilizers account for a significant percentage of the costs associated with crop production, therefore using less fertilizer would reduce the producers' costs. A reduction in fertilizer application would also lessen the environmental damage resulting from extensive nitrogenous fertilizer use. Excess fertilizer application causes increased eutrophication, acid rain, soil acidification and the greenhouse effect. These environmental disasters cause further problems such as fish kills, loss of biodiversity, increased algal blooms, loss of arable land and accelerated global climate change, affecting the world population on both social and economic scales.

Monocots represent a large percentage of the crops grown in the world with approximately 217 million hectares of wheat and 158 million hectares of both maize and rice planted in 2007. Approximately half of the global calorie and protein requirement is derived from wheat, rice and maize. Rice is routinely used as a model crop for genetic and physiological studies in other monocot crops including maize, wheat, sugarcane, barley, sorghum, rye and grass. Rice has a small, diploid genome that is well conserved and syntenic across monocots.

Promoters are nucleic acid sequences that allow for regulation of transcription of a gene or nucleotide sequence. Promoters can allow for constitutive expression, such as the well known cauliflower mosaic virus promoter CaMV 35S, inducible expression, such as the stress inducible promoter rd29A (Pino et al., 2007), tissue specific expression, such as root specific OsANT1 (U.S. Patent Application Publication No. 2009/0288224) and developmentally specific expression, such as the senescence induced IPT promoters (Ma et al., 2009). Promoters can also be weak or strong, suggesting that whenever or wherever they are induced, they will allow for expression of the attached gene or nucleotide sequence at varying levels.

When a promoter is fused to the 5' end of a gene or nucleotide sequence, it can regulate the expression of that gene or nucleotide sequence. However not all promoters will successfully express all genes or nucleotide sequences in all plant types. For example, a dicot promoter may not perform in the same manner when placed in a monocot system, and vice versa. Similarly, a monocot promoter may not function in the same manner when placed in a monocot of a different Genus, such as a rice promoter placed into wheat. For transgenic studies, there are different types of promoters that can be used, depending on the goal of the experiment. Promoters are often classified as constitutive, tissue specific and/or inducible. Many transgenic studies to date have used generic constitutive promoters such as the cauliflower mosaic virus (CAMV35S) and maize ubiquitin 1 promoter (ubi-1) to drive target gene over-expression in plants. This can be a disadvantage as it could be energetically unfavorable for plants to express the gene at all times and it could produce abnormal development, since expression levels of the transgene is not regulated (Shelton et al., 2002). For example, constitutive over-expression of the cellulose synthase like gene CslF6 by the oat globulin promoter ProASGL frequently resulted in reduced germination of seeds or seedlings with necrosis on the leaf tips leading to death in severe cases (Burton et al., 2011).

Using inducible or tissue specific promoters may be a better option to drive transgene expression. Inducible promoters will only drive gene expression when a specific physical, environmental, biological or chemical stimulus is applied. The heat inducible promoter of the Hvhsp17 gene from wheat can be used for high target gene expression when plants are exposed to 38 to 40° C. for 1 to 2 hours (Freeman et al., 2011). This allows for the short term gene or nucleotide sequence expression and control of developmental expression but is limited to tissues that are not severely affected by temperature changes. Over-expression of the *Triticum aestivum* NAC protein (TaNAC69), encoding a transcription factor involved in drought stress by the drought inducible promoter HvDhn4s, produced wheat plants with significantly higher shoot biomass at the early vegetative stage under mild salt stress and water limitation, compared to the wild-type. Conversely, the HvDhn8s constitutive promoter driving TaNAC69 showed no significant difference from untransformed controls (Xue et. al., 2011). When the drought and cold stress inducible promoter rdA29 was used to over-express the DREB1A gene, which encodes a transcription factor involved in stress tolerance in *Arabidopsis*, normal plants were generated, while constitutive expression driven by the CAMV35S promoter resulted in growth retardation under normal growing conditions (Kasuga et al., 1999).

Tissue specific promoters are involved in organ specific and developmental stage specific expression of transgenes. For example, in potatoes, StRCAp is engineered into the leaves as a defense mechanism against predatory insects, but is not expressed in the eating parts of the plant that produces this toxin (Weber, 2003; Park and Jones, 2008). The use of the 35S promoter has also raised concerns of food safety where the toxin produced in non-target organs might cause the potatoes to be unsafe for consumption. In addition, it may be metabolically taxing for the plant to be constantly producing a secondary metabolite, regardless of the developmental stage or organ, therefore causing plants to be less healthy and potentially compromising yields.

In the case of NUE plant engineering, tissue specific expression of genes might increase the efficacy of N uptake, utilization or remobilization in the plant. In contrast, the use of a constitutive promoter might prove to be a waste of energy because over-expression of non-rate limiting enzymes in certain organs may not produce any phenotype or may even decrease yield. Development of an NUE plant may also involve the transformation of multiple genes or gene stacking to achieve a satisfactory NUE phenotype, since N metabolism and transport are very complex processes.

In addition, the use of the CAMV35S promoter may not produce any phenotype because the gene expression or protein expression was not sufficient in a specific organ or developmental phase. Also, plants could turn off the expression of the transgene when it proves to be energetically unfavourable. When HvAlaAT was driven by the CAMV35S promoter, it did not exhibit any NUE phenotype. However, when the root specific btg26 promoter was used, it produced plants that had higher NUE (Good et al., 2007).

Similar to over-expression of target genes, promoters when used in a different species may not mimic the expression patterns of its native species. Seed specific promoters from barley (B-hor and D-hor) and wheat (HMW-Glu) did not direct seed specific expression in rice, instead the promoters drove high expression levels in leaf, shoot and maternal seed tissues of rice plants (Wu et al., 1998; Qu and Takaiwa, 2004; Furtado et al., 2008).

PBpr1 promoters are from genes encoding methyl-melonate semialdehyde dehydrogenase (MMSDH). The PBpr1 promoter is upstream of the OsALDH6 gene, which encodes a gene for methylmalonate semialdehyde dehydrogenase in rice (Accession number: gene: AK 121280.1 and mRNA: AF045770.1). AK121280.1 and AF045770.1 are splice variants of each other where AF045770 is shorter than the AK121280.1. AK121280.1 appears to be a hypothetical protein designated by GenBank, while AF045770.1 has been characterized (Oguchi et al (2004). OsALDH6 is homologous to the ALDH6B2 gene in *Arabidopsis*, which also encodes for a methlymalonate semialdehyde dehydrogenase. The OsALDH6 gene is highly expressed in young roots and stems (Gao and Han, 2009).

Methylmalonate semialdehyde dehydrogenase (MMSDH) catalyzes the irreversible oxidative decarboxylation of malonate semialdehydes to acetyl-CoA and methylmalonate-semialdehyde to propionyl-CoA in the distal portions of the valine and pyrimidine catabolic pathways. Since MMSDH generates acetyl-CoA, it is an important factor in the glyoxylate pathway, TCA cycle and fatty acid production.

MMSDH is down-regulated during oxidative stress due to the restriction in the TCA cycle and the production of ATP (Sweetlove et al., 2002). In two week old rice plants, MMSDH mRNA was found at high levels in roots and leaf sheaths while protein accumulation was found highest in roots followed by leaf blades (Oguchi et al., 2004). With the addition of auxin, MMSDH levels in roots increased along with an increase in rooting. Tanaka et al. (2005) has suggested that MMSDH is involved in root growth, tissue differentiation and thickening growth due to its expression in crown roots, lateral roots and root hairs. MMSDH was found to be localized in the mitochondrial matrix of *Arabidopsis*, rice, human, bovine and rats which suggests a similarity of function of MMSDH among all these organisms.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the invention to provide plants having enhanced nitrogen efficiency. In accordance with one aspect of the present invention, there is provided a transgenic plant or plant part comprising a polynucleotide encoding a nitrogen utilization protein operably linked to a PBpr1 promoter.

In accordance with another aspect, there is provided a seed obtained from a transgenic plant of the invention.

In accordance with another aspect of the invention, there is provided a plant cell transformed with a polynucleotide encoding a nitrogen utilization protein operably linked to a PBpr1 promoter.

In accordance with another aspect of the invention, there is provided a genetic construct comprising a polynucleotide encoding a nitrogen utilization protein operably linked to a PBpr1 promoter.

In accordance with another aspect, there is provided a vector comprising a genetic construct of the invention.

In accordance with another aspect, there is provided a host cell comprising a genetic construct or a vector according of the invention.

In accordance with another aspect of the invention, there is provided a method of generating a plant having increased nitrogen use efficiency comprising: transforming a plant cell with a genetic construct or vector of the invention, and growing the transformed plant cell to produce a plant that expresses the nitrogen utilization protein from the PBpr1 promoter, thereby generating a plant having increased nitrogen use efficiency, wherein the increased nitrogen use efficiency is relative to the nitrogen use efficiency of a wild-type plant grown under identical conditions.

In accordance with another aspect of the invention, there is provided a method of generating a plant having increased biomass comprising:

transforming a plant cell with a genetic construct or vector of the invention, and growing the transformed plant cell to produce a plant that expresses the nitrogen utilization protein from the PBpr1 promoter, thereby generating a plant having increased biomass, wherein the increased biomass is relative to the biomass of a wild-type plant grown under identical conditions.

In accordance with another aspect of the invention, there is provided a method of generating a plant having increased seed yield comprising: transforming a plant cell with a genetic construct or vector of the invention, and growing the transformed plant cell to produce a plant that expresses the nitrogen utilization protein from the PBpr1 promoter, thereby generating a plant having increased seed yield, wherein the increased seed yield is relative to the seed yield of a wild-type plant grown under identical conditions.

In accordance with another aspect of the invention, there is provided a method for producing a plant having increased nitrogen use efficiency, increased biomass, increased seed yield, or a combination thereof, comprising: (a) providing a plant, a plant part or a seed comprising a genetic construct or vector of the invention, and (b) growing a plant from the plant, plant part or seed, thereby producing a plant having increased nitrogen uptake, increased biomass, increased seed yield, or a combination thereof, wherein the increased nitrogen uptake, increased biomass and increased seed yield is relative to the nitrogen uptake, biomass and seed yield of a wild-type plant grown under identical conditions.

In accordance with another aspect, there is provided a use of a transgenic plant of the invention for producing progeny.

In accordance with another aspect of the invention, there is provided a use of a genetic construct or vector of the invention to increase nitrogen use efficiency, biomass or seed yield in a plant.

In accordance with another aspect of the invention, there is provided a process for increasing nitrogen use efficiency, biomass, seed yield, or a combination thereof, in a plant comprising: providing a seed comprising a genetic construct or the vector of the invention, applying a herbicide, insecticide, fertilizer, or combination thereof, to the seed, and growing a plant from the seed, wherein the plant has increased nitrogen use efficiency, increased biomass, increased seed yield, or a combination thereof, and wherein the increased nitrogen use efficiency, increased biomass or increased seed yield is relative to the nitrogen use efficiency, biomass or seed yield of a wild-type plant grown under identical conditions.

In certain embodiments, the present invention provides a method of generating the plant with increased nitrogen use efficiency comprising, introducing a nucleic acid encoding the one or more nitrogen utilization protein operably linked to a root-epidermis-specific promoter, and producing the plant, the plant comprising elevated levels of one or more nitrogen utilization protein specifically localized to the root epidermis.

In certain embodiments, the present invention provides a method for directing tissue-specific expression of a target gene or nucleotide sequence in a plant, including producing a plant from a transformed plant cell such that tissue-specific expression of a target gene or nucleotide sequence occurs within a selected tissue of the plant, wherein the transformed plant cell contains a target gene or nucleotide sequence in operative linkage with a PBpr1 promoter element. In one embodiment, the tissue-specific expression takes place in the root of the plant.

In certain embodiments, the present invention provides a method for directing tissue-specific and environmental or developmentally-regulated expression of a target gene or nucleotide sequence in a plant, including producing a plant from a transformed plant cell such that tissue-specific and environmentally or developmentally-regulated expression of a target gene or nucleotide sequence occurs within a selected tissue of the plant, wherein the transformed plant cell contains a target gene or nucleotide sequence in operative linkage with a PBpr1 promoter element. In one embodiment, the tissue-specific expression takes place in the root or leaves of the plant and the environmentally or developmentally-regulated expression takes place under conditions of nutrient stress.

In certain embodiments, the present invention provides a method for increasing biomass of a plant growing under one or more environmentally adverse conditions comprising; transforming a plant with a target gene or nucleotide sequence in operative linkage with a PBpr1 promoter element to produce a transformed plant, the target gene or nucleotide sequence encoding an enzyme involved in nitrogen assimilation or metabolism; and growing the transformed plant. In one embodiment, the enzyme is alanine aminotransferase (AlaAT).

In certain embodiments, the present invention provides a method for increasing biomass of a plant growing under conditions of low nitrogen comprising; transforming a plant with a target gene or nucleotide sequence in operative linkage with a PBpr1 promoter element to produce a transformed plant, the target gene or nucleotide sequence encoding an enzyme involved in nitrogen assimilation; and growing the transformed plant. In one embodiment, the enzyme is AlaAT.

In certain embodiments, the present invention provides a method for increasing the biomass of a plant growing under one or more environmentally adverse conditions comprising; transforming a plant with a gene or nucleotide sequence encoding AlaAT in operative linkage with a promoter element to produce a transformed plant; and growing the transformed plant. In one embodiment, the promoter is PBpr1.

In certain embodiments, the present invention provides a method for increasing seed yield of a plant comprising; transforming the plant with a target gene or nucleotide sequence or nucleotide sequence in operative linkage with a PBpr1 promoter element, to produce a transformed plant, the target gene or nucleotide sequence or nucleotide sequence encoding an enzyme involved in nitrogen assimilation or metabolism; and growing the transformed plant. In one embodiment, the enzyme is AlaAT.

In certain embodiments, the present invention provides a method for increasing seed yield of a plant growing under conditions of low nitrogen comprising; transforming a plant with a target gene or nucleotide sequence or nucleotide sequence in operative linkage with a PBpr1 promoter element to produce a transformed plant, the target gene or nucleotide sequence or nucleotide sequence encoding an enzyme involved in nitrogen assimilation; and growing the transformed plant. Preferably, the enzyme is AlaAT.

In certain embodiments, the present invention provides a method for increasing seed yield of a plant growing under conditions of high nitrogen comprising; transforming a plant with a target gene or nucleotide sequence or nucleotide sequence in operative linkage with a PBpr1 promoter element to produce a transformed plant, the target gene or nucleotide sequence or nucleotide sequence encoding an enzyme involved in nitrogen assimilation; and growing the transformed plant. In one embodiment, the enzyme is AlaAT.

This summary of the invention does not necessarily describe all features of the invention and is not intended to be limiting.

BRIEF DESCRIPTION OF THE DRAWINGS

These and other features of the invention will become more apparent from the following description in which reference is made to the appended drawings.

FIG. 5 shows (A) $T_3$ PBpr1 plant dry above ground biomass (g) at 52 DAG, each line was represented by 5 replication plants and error bars are SD, and (B) the fresh weight (g) of three PBpr1:AlaAT over-expressing rice lines versus WT (NB; Nipponbare) at maturity during soil growth conditions.

FIG. 13 shows the nucleotide sequence of the PBpr1 promoter in double stranded annotation including the ATG start and initial nucleotides of the coding sequence (SEQ ID NO: 6) and showing the EcoRI and SacI restriction enzyme sites used for cloning. The lower nucleotide strand represents the reverse complement of SEQ ID NO: 6.

The nucleotide sequence of the barley (*Hordeum vulgare*) AlaAT gene is represented in SEQ ID NO:2 and the amino acid sequence of the AlaAT protein is represented in SEQ ID NO:3.

Figure 14:
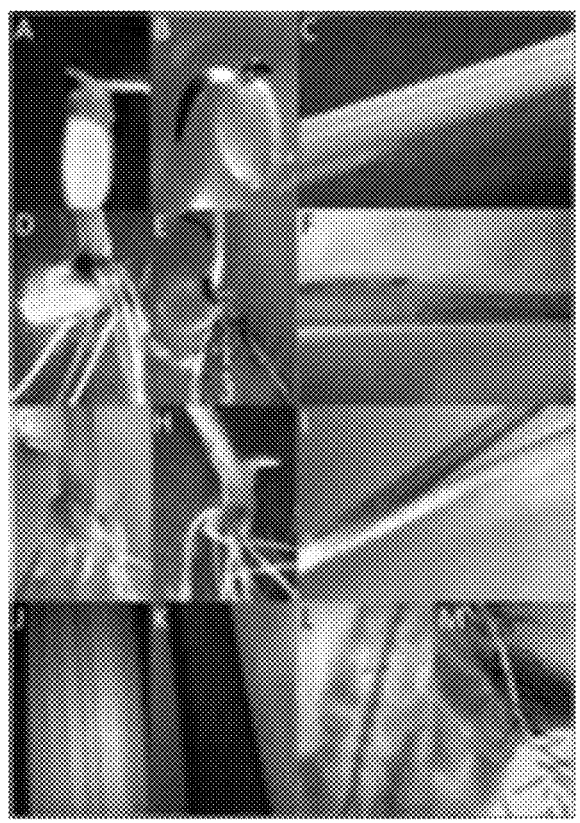

FIG. 14 shows GUS staining of (A) 3 day old PBpr1:GUSplus (PBpr1G line) seedling, (B) 3 day old OsANT1::GUSplus (OsANT1::GUS lines) seedling as a positive control. (C) to (M) are GUS stained tissues from 7 to 10 day old seedlings of PBpr1G and OsANT1::GUS lines. (C) stem of PBpr1G, (D), (G), and (H) basal region of the shoot/shoot root interface containing remnant seed PBpr1 G, (E) basal region of the shoot/shoot root interface containing remnant seed OsANT1GUS, (F) stem of OsANT1GUS, (I) leaf sheath and leaf blade interface OsANT1GUS, (J) leaf blades and veins PBpr1G, (K) leaf blades and veins OsANT1GUS, (L) roots and root hairs PBpr1G, and (M) roots and root hairs OsANT1GUS.

FIG. 15 presents a table showing the foliar amino acid concentrations of wildtype (cv. Nipponbare) rice versus barley AlaATover-expressing rice transgenic rice lines; AGR 1/7 (OsANT1:HvAlaAt) and PBpr1-11, PBpr1-12, PBpr1-21 (OsPBpr1:HvAlaAT). Amino acid concentration (nM/g FW) are averages of 4 replicates.

FIG. 16 shows (A) PBpr2 promoter driving expression of AlaAT in rice, T1 generation, grown in soil growth chamber; comparison of plant height, total biomass and seed weight to wild-type rice cv. Nipponbare (NB), and (B) PBpr2 promoter driving expression of AlaAT in rice, T2 generation, grown in soil growth chamber; comparison of total biomass and seed weight to wild-type rice cv. Nipponbare (NB).

The nucleotide sequence of the PBpr1 promoter is shown in SEQ ID NO: 1, and the nucleotide sequence of the PBpr2 promoter is shown in SEQ ID NO: 4.

Figure 17:
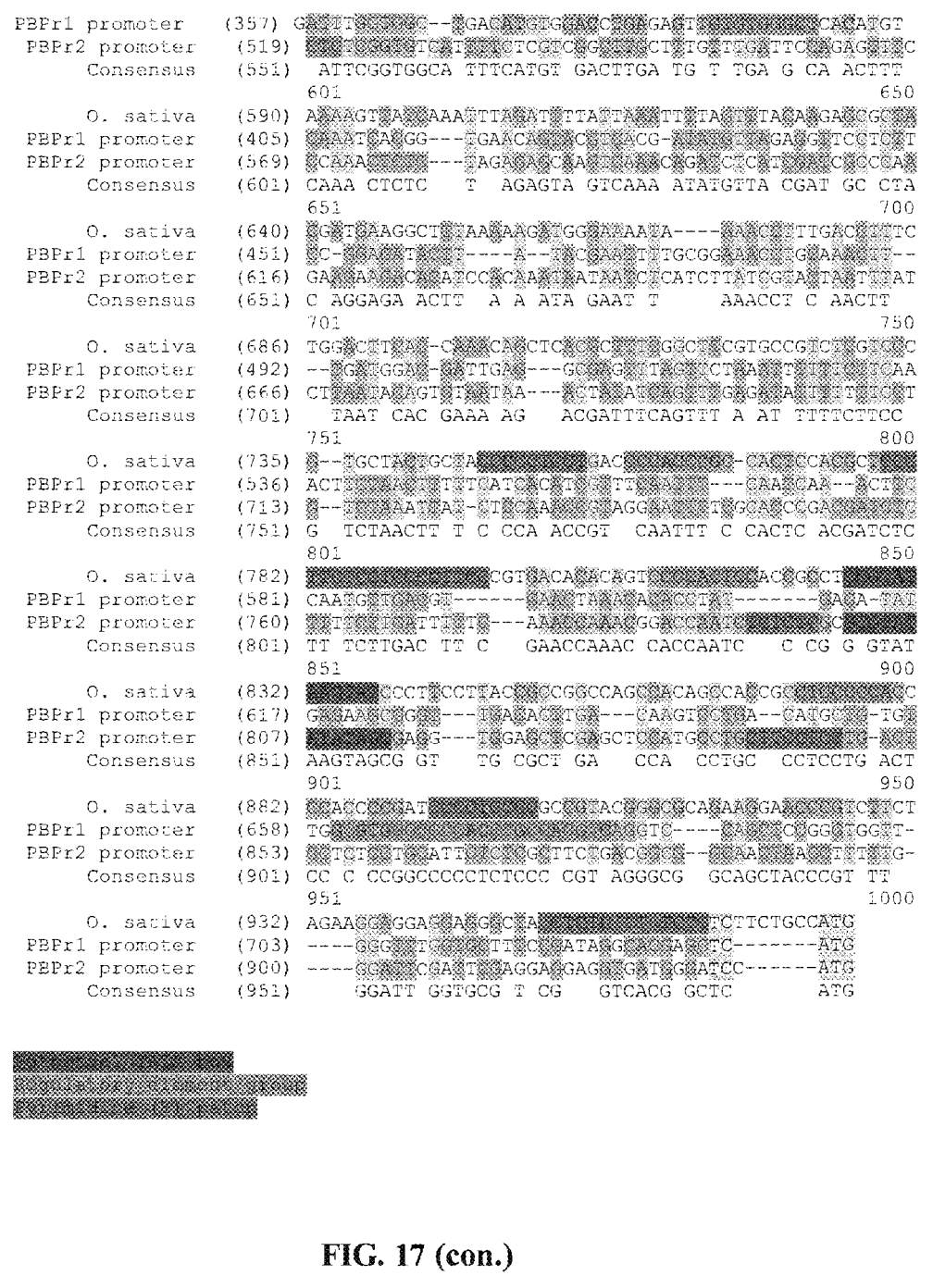

FIG. 17 shows an alignment of the nucleotide sequences of the OsANT1 promoter (SEQ ID NO:5), the PBpr1 promoter (SEQ ID NO:1) and the PBpr2 promoter (SEQ ID NO:4).

DETAILED DESCRIPTION OF THE INVENTION

The present invention relates to monocot plants having enhanced yield and/or nitrogen utilization efficiency (NUE), to methods for enhancing yield and NUE in monocot plants, and to methods of increasing biomass and seed yield in monocot plants. This invention also relates to PBpr1 promoters, which are promoters from genes encoding methylmelonate semialdehyde dehydrogenase (MMSDH).

Given the worldwide requirements for monocots and the diminishing fertility of existing fields, it is desirable to generate monocot plants that are able to grow under suboptimal nutrient conditions. One means for accomplishing this goal is to generate monocot plants that can use nitrogen more efficiently. Such monocot plants have the advantage of being able to grow in soils that are poorer in nitrogen, as a result of being able to more efficiently use the nitrogen that is available, with no loss in yield. Additionally, such monocot plants may also demonstrate enhanced yield in soils that have normal nitrogen levels as well. Nitrogen use efficiency in plants is a result of two main subcomponents; N uptake efficiency and N utilization efficiency. A plant exhibiting a nitrogen use efficiency phenotype may have improvements in its' ability to take up nitrogen from the soil, which is a desired trait in plants growing in lower nutrient-available soils. Or the NUE plant may have improvements in its' ability to utilize the N that it has taken up so that the available N (whether it be low or high) is efficiently incorporated into the subcellular components (such as nucleic acids, proteins, storage etc.), translocated to the necessary tissues and remobilized at the correct developmental stage into seed. Or, another possibility is that the NUE plant has improvements in both N uptake and utilization. Any one of these possibilities would allow for an increased yield from a NUE crop grown in normal nitrogen conditions because those plants would be able to take up a non-limiting amount of nitrogen and be able to use the nitrogen to increase biomass and seed yield, either by increased number of seeds or an increase in seed weight, or both. Certain embodiments of the invention provide for transgenic plants having improved nitrogen utilization efficiency compared to wild-type plants.

Plants face a wide variety of non-optimal environmental conditions during growth and development. Such conditions may include water limitation, excess salinity, alkaline or acidic soil, infestation by pests, disease, or temperature stress, any of which individually may significantly hinder crop growth and/or yields. Certain embodiments of the present invention provide methods by which plants, and seeds thereof, may be engineered to grow and thrive under changing environmental conditions usually not conducive to the development of the plant. In some embodiments, methods are provided to develop plants that can maintain or increase their biomass and yield while being grown under conditions that are not optimal, in terms of nutrient applications are described.

In certain embodiments, the present invention advantageously allows the user to develop plants that have an environmental benefit in that they can maintain yield, while reducing the need for high levels of nutrient application. In certain embodiments, the present invention allows the user to develop plants that, under high nutrient levels, have improved nutrient up-take allowing the plants to extract more nutrients from their environment during times of nutrient abundance. Using the methods and compositions of certain embodiments of the invention, plants may be improved for growth and development under environmental conditions usually unsuitable for growth of the plant. In some embodiments, the methods and compositions of the invention permit the genetic engineering of a plant to alter one or more plant characteristics in only selected tissues of the plant.

Unless defined otherwise, all technical and scientific terms used herein have the same meaning as commonly understood by one of ordinary skill in the art to which this invention belongs.

As used herein, the terms "comprising," "having," "including" and "containing," and grammatical variations thereof, are inclusive or open-ended and do not exclude additional, unrecited elements and/or method steps. The term "consisting essentially of" when used herein in connection with a composition, use or method, denotes that additional elements and/or method steps may be present, but that these additions do not materially affect the manner in which the recited composition, method or use functions. The term "consisting of" when used herein in connection with a composition, use or method, excludes the presence of additional elements and/or method steps. A composition, use or method described herein as comprising certain elements and/or steps may also, in certain embodiments consist essentially of those elements and/or steps, and in other embodiments consist of those elements and/or steps, whether or not these embodiments are specifically referred to.

In addition, the use of the singular includes the plural, and "or" means "and/or" unless otherwise stated.

As used herein, the term "about" refers to an approximately +/−10% variation from a given value. It is to be understood that such a variation is always included in any given value provided herein, whether or not it is specifically referred to.

The term "substantially identical" as used herein in relation to a nucleotide or amino acid sequence indicates that, when optimally aligned, for example using the methods described below, the nucleotide or amino acid sequence shares at least 70%, at least 75%, at least 80%, at least 85%, at least 90%, at least 95%, at least 96%, at least 97%, at least 98% or at least 99% sequence identity with a defined second nucleotide or amino acid sequence (or "reference sequence"). "Substantial identity" may be used to refer to various types and lengths of sequence, such as full-length sequence, functional domains, coding and/or regulatory sequences, promoters, and genomic sequences. Percent identity between two amino acid or nucleotide sequences can be determined in various ways that are within the skill of a worker in the art, for example, using publicly available computer software such as Smith Waterman Alignment (Smith, T. F. and M. S. Waterman (1981) *J Mol Biol* 147:195-7); "BestFit" (Smith and Waterman, *Advances in Applied Mathematics*, 482-489 10 (1981)) as incorporated into GeneMatcher Plus™, Schwarz and Dayhof (1979) *Atlas of Protein Sequence and Structure*, Dayhof, M. O., Ed pp 353-358; BLAST™ program (Basic Local Alignment Search Tool (Altschul, S. F., W. Gish, et al. (1990) J Mal Biof 215: 403-10), and variations thereof including BLAST-2, BLAST-P, BLAST-N, BLASTX, WU-BLAST-2, ALIGN, ALIGN-2, CLUSTAL, and Megalign (DNASTAR) software. In addition, those skilled in the art can determine appropriate parameters for measuring alignment, including algorithms needed to achieve maximal alignment over the length of the sequences being compared. In general, for amino acid sequences, the length of comparison sequences will be at least 10 amino acids. One skilled in the art will understand that the actual length will depend on the overall length of the sequences being compared and may be at least 20, at least 30, at least 40, at least 50, at least 60, at least 70, at least 80, at least 90, at least 100, at least 110, at least 120, at least 130, at least 140, at least 150, or at least 200 amino acids, or it may be the full-length of the amino acid sequence. For nucleotide sequences, the length of comparison sequences will generally be at least 25 nucleotides, but may be at least 50, at least 100, at least 125, at least 150, at least 200, at least 250, at least 300, at least 350, at least 400, at least 450, or at least 500, or it may be the full-length of the nucleotide sequence.

The term "tissue-specific expression" of a target nucleotide sequence is known in the art and includes the expression of a target nucleotide sequences predominantly in selected tissues. Tissue-specific expression may result in expression of the target nucleotide sequence only in the selected tissue, in which case the target nucleotide sequence may be present in multiple tissues, but is expressed in only a subset of those tissues. Alternatively, tissue-specific expression may result in higher levels of expression of the target nucleotide sequence in selected tissues, in which case expression may also be observed in other tissues, but at a lower level than in the target tissue(s), for example, 50% lower, 40% lower, 30% lower, 25% lower or 20% lower. Such selective expression may be due to the influence of one or more regulatory genetic elements, for example but not limited to promoter elements, repressor elements, enhancer elements, or other regulatory factors that may interact with DNA, RNA.

The terms "target gene" or "target nucleotide sequence" are art-recognized, and include nucleotide sequences which are desired to be expressed in one or more selected plant tissues. Non-limiting examples of target genes or nucleotide sequences which may be utilized in conjunction with the methods of the invention include genes or nucleotide sequences involved in nitrogen assimilation and/or utilization, genes or nucleotide sequences involved stress resistance, genes or nucleotide sequences disease and pest resistance, and genes or nucleotide sequences involved in nutrient uptake and utilization. Such genes or nucleotide sequences are well known to one of skill in the art.

The terms "operative linkage," "operatively linked" and "operably linked" are used interchangeably herein to refer to the placement of a target nucleotide sequence relative to a nucleic acid regulatory sequence such that the expression of the target nucleotide sequence is controlled by the regulatory sequence. This regulatory sequence can have a positive effect (increase) on the expression of the target gene or nucleotide sequence (e.g., the regulatory sequence is a promoter or an enhancer element), or the regulatory sequence can reduce the expression of the target gene or nucleotide sequence (e.g., the regulatory sequence is a repressor element). The regulatory sequence may be physically located 5' or 3' of the target gene or nucleotide sequence, may be within the coding sequence of the target gene or nucleotide sequence, or may be contained on an intron within the target gene or nucleotide sequence.

The term "nulls" is art-recognized and includes a plant that has undergone tissue culturing but does not carry a transgene or selectable marker.

Production of plants which express one or more target genes or nucleotide sequences in a tissue-specific fashion are described herein. In certain embodiments, invention provides seeds containing one or more target genes or nucleotide sequences under the control of a promoter element which specifically directs the tissue-specific expression of the gene or nucleotide sequence. In certain embodiments, the methods of the invention allow production of plants having one or more desired traits or properties in selected tissues; e.g., to alter specifically the genetic and/or physiological properties of the fruit or the roots of the plant. Certain embodiments of the invention further provide methods of producing plants having root and leaf-specific expression of one or more desired nucleotide sequences using the PBpr1 promoter element.

The methods of the invention for the production of plants having tissue-specific expression of one or more target genes or nucleotide sequences are accomplished through the use of a genetic regulatory element which directs the tissue-specific expression of the target gene(s). Regulatory elements may be either negative or positive in activity: a plant tissue-specific promoter or enhancer element permits the expression of the target gene or nucleotide sequence(s) in one or more specific tissues, whereas a plant tissue-specific repressor suppresses the expression of the target genes or nucleotide sequences in one or more specific tissues, while expression in the other tissue(s) continues unabated. For the purposes of the invention, it will be understood that promoter sequences constitute the preferred genetic regulatory elements of the invention.

The tissue-specific promoters useful in the present invention can be either homologous or heterologous to the plant to which they are to be used. Promoters which direct the expression of an operatively linked gene or nucleotide sequence in one or more plant tissues while excluding expression of the linked gene or nucleotide sequence in one or more other plant tissues may be used in the methods and constructs of the invention. Appropriate plant tissues include but are not limited to e.g., root, leaf, petal, sepal, stamen, anther, stigma, ovary, style, pistil, epidermis, phloem, xylem, cortex, pith, cambium, stem or trunk, root hair, petiole, fruit and tuber.

Preferably, the promoter is a PBpr1 promoter. In accordance with certain embodiments of the invention, the promoter is a PBpr1 promoter having a nucleotide sequence substantially identical to the sequence as set forth in SEQ ID NO: 1 (FIG. 13).

It will be understood by one skilled in the art that modifications may be made to the promoters useful in the methods and constructs of the invention to improve or modulate the activity of the promoter. Multiple copies of a selected promoter may be operatively linked to a single target gene or nucleotide sequence to thereby alter the expression level of the linked gene or nucleotide sequence, or a selected promoter may be operatively linked to one or more target genes or nucleotide sequences such that the expression of each target gene or nucleotide sequence is coordinately regulated. A promoter may be of any size appropriate to permit the tissue-specific functioning of the promoter. A promoter may be modified (e.g., by mutagenesis, deletion, insertion, or truncation) to alter the degree to which the operatively linked gene or nucleotide sequence is expressed in the selected tissue, or to alter the specificity of tissue expression directed by the promoter. Further, the placement of the promoter relative to the operatively linked target gene or nucleotide sequence may be modulated (e.g., moved further away or closer together) to attain a desired level of promoter-directed expression.

A promoter may direct the expression of an operatively linked gene or nucleotide sequence in one or more selected tissues of the plant, and also direct expression of the gene or nucleotide sequence in response to a specific environmental or physiological condition. For example, promoters may be activated under conditions of stress (e.g., drought stress, saline stress, temperature stress, oxygen stress, pH stress, or heavy metal stress), under conditions of nutrient deprivation, under conditions of attack by disease or pests. In another example, promoters may be activated under specific developmental conditions (e.g., upon sprouting, fruiting, or seed production) or in response to a change in environmental conditions (e.g., from nutrient deprivation to provision or from hypoxia to normoxia).

In certain embodiments, the present invention provides for constructs comprising a target gene under control of a PBpr1 promoter that, when transformed into an appropriate plant host, result in tissue-specific expression of the gene product. For example, expression may preferentially be in the roots and/or shoots of the plant. In certain embodiments, the present invention provides for constructs comprising a target gene under control of a PBpr1 promoter that, when transformed into an appropriate plant host, result in developmentally regulated expression of the gene product.

A target gene or nucleotide sequence of the invention is a gene or nucleotide sequence which it is desired to be expressed in a plant. General classes of target genes or nucleotide sequences which may be advantageously employed in the methods and constructs of the invention include genes or nucleotide sequences encoding plant structural proteins, genes or nucleotide sequences encoding proteins involved in the transport and/or uptake of nutrients, genes or nucleotide sequences encoding enzymes and proteins involved in nutrient utilization, genes or nucleotide sequences encoding proteins involved in plant resistance to herbicides, genes or nucleotide sequences encoding proteins involved in plant resistance to nematodes, viruses, insects, or bacteria, genes or nucleotide sequences encoding proteins involved in plant resistance to stress (e.g., osmotic, temperature, pH, or oxygen stress), genes or nucleotide sequences encoding proteins involved in stimulation or continuation of plant growth, or genes or nucleotide sequences encoding proteins involved in phytoremediation. Further, the target gene or nucleotide sequence may be a nucleotide sequence which, when transcribed, is antisense to a native sequence, the transcription and translation of which is desired to be suppressed.

In certain embodiments of the invention, the target genes or nucleotide sequences are those encoding enzymes in the assimilation and/or metabolism of nitrogen. The genes or nucleotide sequences of interest may include genes or nucleotide sequences which encode proteins involved in assimilating ammonia into amino acids or use the formed amino acids in biosynthetic reactions, that is, "nitrogen utilization proteins". Examples of nitrogen utilization proteins include, but are not limited to, nitrate ammonium and amino acid transporters, glutamine synthetase (GS), asparagine synthetase (AS), glutamate synthase (also known as glutamate 2:oxogluturate amino transferase and GOGAT), asparaginase (ANS), glutamate dehydrogenase (GDH), aspartate aminotransferase (AspAT) and alanine aminotransferase (AlaAT) and those genes or nucleotide sequences which may be involved in Nutrient Use Efficiency (NUE) as described by Beatty et al. (2009), and in U.S. Pat. No. 7,589,257. Sequences of appropriate target genes and nucleotide sequences are readily available from public sources, for example GenBank, or can be determined by standard techniques well-known to those of skill in the art.

The target gene or nucleotide sequence may be a gene or nucleotide sequence naturally expressed in the selected plant, or it may be heterologous to the selected plant. The gene or nucleotide sequence may originate from a variety of sources, including viral, bacterial, plant or animal sources.

Certain embodiment of the invention provide for genetic constructs comprising the target gene or nucleotide sequence operably linked to a PBrp1 promoter. In certain embodiments, the gene or nucleotide sequence is heterologous to the PBrp1 promoter to which it is linked.

The target gene or nucleotide sequence can be modified as required. For example, the gene or nucleotide sequence is modified to be transcribable and translatable in a plant system, for example by codon optimization. In certain embodiments, the gene or nucleotide sequence can be modified such that it contains all of the necessary poly-adenylation sequences, start sites and termination sites which allow the coding sequence to be transcribed into messenger ribonucleic acid (mRNA) and the mRNA to be translated into a functional protein in the selected plant system.

Certain embodiments of the invention thus provide for genetic constructs comprising the target gene or nucleotide sequence operably linked to a PBrp1 promoter and further comprising one or more poly-adenylation sequences, transcription start sites, and/or transcription termination sequences. Such target gene or nucleotide sequence modifications and the methods by which they may be made are well known in the art. In certain embodiments, the target gene or nucleotide sequence encodes a nitrogen utilization protein, for example, a nitrate transporter, an ammonium transporter, an amino acid transporter, glutamine synthetase (GS), asparagine synthetase (AS), glutamate synthase (also known as glutamate 2:oxogluturate amino transferase and GOGAT), asparaginase (ANS), glutamate dehydrogenase (GDH), aspartate aminotransferase (AspAT), or alanine aminotransferase (AlaAT). Other examples include those genes or nucleotide sequences which may be involved in Nutrient Use Efficiency (NUE) as described by Beatty et al. (2009), and in U.S. Pat. No. 7,589,257.

In certain embodiments, the present invention provides for vectors comprising the genetic constructs. One skilled in the art will appreciate that the precise vector used is not critical to the instant invention and suitable vectors can be readily selected by the skilled person. Examples of expression vectors and cloning vehicles include, but are not limited to, viral particles, baculovirus, phage, plasmids, phagemids, cosmids, fosmids, bacterial artificial chromosomes, retrovirus vectors, viral DNA (for example, vaccinia, adenovirus, foul pox virus, pseudorabies and derivatives of SV40), P1-based artificial chromosomes, yeast plasmids, yeast artificial chromosomes, and other known vectors specific for specific host cells of interest.

Certain embodiments provide for host cells comprising the genetic constructs or vectors according to the invention. The genetic construct or vector can be introduced into a suitable host cell by one of a variety of standard methods. Such methods are well-known in the art and include, for example, stable or transient transfection, lipofection, electroporation, and infection with recombinant viral vectors. One skilled in the art will understand that selection of the appropriate host cell will be dependent upon the vector chosen. Examples of host cells include, but are not limited to, bacterial, yeast, insect, plant and mammalian cells. In certain embodiments, the host cell is a plant cell.

The methods and genetic constructs disclosed herein may be used to produce a plant or a plant part of any species capable of utilizing the promoter such that the transgenic (non-natural) plant, has tissue-specific expression of one or more desired genes or nucleotide sequences. The invention is intended to be particularly applicable to, for example, crop plants (especially those of the genus *Oryza*), ornamental plants, and trees (particularly conifers and the genus *Populus*). Particularly suitable plants for the practice of the present invention include, but are not limited to, canola, barley, sugar cane, corn, canola, tobacco, soybean, cotton, alfalfa, tomato, wheat, potato, aspen, cottonwood, conifers and poplar, or parts of any of these plants, for example, roots, root tips, leaves, stems, flowers, apical buds, meristematic tissues, and the like. In certain embodiments, plants for use in the invention include canola, barley, maize, rice, tobacco, soybean, cotton, alfalfa, tomato, wheat, potato, and certain tree genera, including conifers and *Populus* species.

In certain embodiments, the methods, uses and constructs of the invention are applied to plants of the genus *Oryza* and other genera closely related to *Oryza*, such as *Porteresia* and *Leersia*. Examples of species in these genera include, but are not limited to, *Oryza sativa*, *Oryza punctata*, *Oryza officinalis*, *Oryza malapuzhanensis*, *Oryza latifolia*, *Oryza australiensis*, *Oryza brachyantha*, *Oryza granulate*, *Oryza longiglumis*, *Oryza schlechteri*, *Porteresia coarctata*, *Leersia perrieri*, *Leersia hexandra* and *Leeria tisserantti*.

The transgenic (non-natural) plants, plant parts, and seeds produced according to the present invention may be further useful in breeding programs for the production of plant species having more than one desired trait. For example two transgenic plants of the invention each having expression of a desired transgene in differing plant tissues may be crossed to result in progeny transgenic plants having tissue-specific expression of both transgenes; or two transgenic plants of the invention each having expression of a different desired transgene in the same plant tissue may be crossed to result in progeny transgenic plants having tissue-specific expression of both transgenes. In this fashion it is possible to produce transgenic plants having a combination of desirable traits in selected tissue(s) of the plant.

Furthermore, it will be understood by one skilled in the art that different species of plants may be more or less amenable to genetic manipulation in general, and that, therefore, it may be advantageous to first transform a related species of the desired plant by the methods and with the constructs of the invention and to subsequently introduce the tissue-specific expression of the target gene or nucleotide sequence into the desired plant species by cross-breeding techniques. Such techniques and appropriately related plant species are well known to one skilled in the art.

Plant cells or protoplasts that have been transformed with the gene construct of the present invention can be regenerated into differentiated plants using standard nutrient media supplemented with shoot-inducing or root-inducing hormone, using methods known to those skilled in the art (see, for example, U.S. Pat. No. 4,634,674 and references therein). Seeds may additionally be harvested from such transgenic plants using methods well known in the art and further used to re-grow the transgenic plants and hybrids of the invention.

Uses

The methods and constructs of the invention allow the production of plants and seeds having expression of one or more desired genes or nucleotide sequences, for example, in one or more selected tissues of the plant. Thus, in certain embodiments, the methods and constructs of the invention permit the production of plants having one or more desired traits limited to selected plant tissues, thereby enabling the targeting of a trait to the tissue to which it is best suited, or avoiding the expression of a desirable gene or nucleotide sequence in a tissue where its effects are unwanted. There are a wide variety of specific applications of the invention, including, but not limited to, the production of plants having increased yield, stress tolerance, having improved nutrient uptake and/or utilization, having improved nutrient content and/or yields of desired compounds, and having phytoremediative properties. Specific applications of the invention are further described below.

One application of the invention is in the production of plants better able to thrive on nutrient-poor soils. It is well known in the art that certain plant species, particularly crop plants, deplete the soil of nutrients necessary to sustain growth, such as nitrogen, phosphate, and potassium. In order to replenish the lacking nutrients, it is necessary either to fertilize the soil (an expensive and environmentally damaging procedure) or to cultivate plants known to deposit the depleted nutrient into the soil (e.g., clover or soybean in the case of nitrogen depletion), which may be crops that are less profitable or nutritive and therefore less desirable to grow. Frequent fertilizing to maintain optimal nutrients in the soil is costly in terms of agriculture outputs such as labour and fuel therefore crop plants are usually in a state of either nutrient abundance or depletion. Another application of the invention is in the production of plants better able to capture and utilize nitrogen when it is present in either an adequate or abundant supply in the soil before nitrogen loss due to leaching, volatilization or microbial degradation occurs.

In certain embodiments, the methods of the invention permit the targeted expression of genes or nucleotide sequences involved in nutrient uptake (e.g., transport molecules) to those tissues in which the uptake occurs (e.g., the root or root hairs) to thereby improve the ability of the plant to absorb the nutrient from the environment. In some embodiments, the invention may be used to produce plants which express heterologous nutrient utilization nucleotide sequences, or optimized (for example, optimized for plant expression) native nutrient utilization nucleotide sequences, that permit more efficient use of the nutrient, such that less of the nutrient is required for the normal growth and functioning of the plant. In certain embodiments, the expression of such sequences is targeted to selected tissues (e.g., the root or leaves). In certain embodiments, the methods of the invention allow for expression of genes or nucleotide sequences involved in the use and uptake of nutrients not normally used by the plant in those plant tissues which are directly exposed to the different nutrient (e.g., root and leaf). In this fashion, plants which are able to grow and thrive on different nutrient sources (e.g., different nitrogen sources) may be produced. Particularly useful target genes or nucleotide sequences for the optimization of nitrogen efficiency of the plant include: nitrate transporters, ammonia transporters and amino acid transporters, glutamine synthetase (GS), asparagine synthetase (AS), glutamate synthase (also known as glutamate 2:oxogluturate amino transferase and GOGAT), asparaginase (ANS), glutamate dehydrogenase (GDH), alanine dehydrogenase, aspartate aminotransferase (AspAT) and alanine aminotransferase (AlaAT) and those genes or nucleotide sequences which may be involved in Nutrient Use Efficiency described by Beatty et al. (2009), and U.S. Pat. No. 7,589,257.

In certain embodiments, plants produced by the methods of the invention can more efficiently utilize fertilizer input by rapidly taking up the nitrogen in the fertilizer and storing it at the time of application, to thereby reduce the amounts of nitrogenous fertilizer which are lost to leaching, etc. This may permit a reduction in the amount of nitrogenous fertilizer required to be applied to a crop, to obtain crop yields comparable to those obtained using normal cultivation techniques and plants which have not been modified according to the present invention. Additional agronomic advantages can include faster growth and crop yield, where nitrogenous fertilizer input is maintained at levels used in common crop cultivation techniques.

Development of Cereal Crops

As described below, transformed *Oryza sativa* plants ectopically expressing a nucleotide sequence encoding an enzyme involved in nitrogen assimilation or metabolism, for example but not limited to alanine dehydrogenase, glutamine synthetase, asparagine synthetase, glutamate synthase, asparaginase, glutamate dehydrogenase, aspartate aminotransferase, alanine aminotransferase, and those nucleotide sequences which may be involved in Nutrient Use Efficiency described by Beatty et al. (2009), and U.S. Pat. No. 7,589,257 were developed using a PBpr1 promoter and grown under laboratory conditions to determine if the beneficial effects on plant growth and yield under controlled growth conditions could be obtained. For example, it was examined whether the amount of available nitrogen would have an effect on plant biomass and seed yield on plants expressing PBpr1/AlaAT grown under laboratory conditions when compared to similar plants that did not ectopically express the target nucleotide sequence.

Seed yield in control and transgenic plants grown under laboratory conditions was examined. Transgenic plants expressing a gene or nucleotide sequence encoding an enzyme involved in nitrogen assimilation or metabolism exhibited higher biomass and seed yields than control plants in the presence of an adequate supply of nitrogen. Collectively these results indicate that transgenic plants ectopically expressing an enzyme involved in nitrogen assimilation or metabolism are capable of optimising the utilization of available nitrogen under a range of environmental conditions thereby resulting in an increase in plant biomass, seed yield or a combination thereof.

Therefore, in one aspect, the present invention provides a method for increasing seed yield of a plant comprising; transforming the plant with a target gene or nucleotide sequence in operative linkage with a PBpr1 promoter element, to produce a transformed plant, the target gene or nucleotide sequence encoding an enzyme involved in nitrogen assimilation or metabolism; and growing the transformed plant.

The above description is not intended to limit the claimed invention in any manner, furthermore, the discussed combination of features might not be absolutely necessary for the inventive solution.

To gain a better understanding of the invention described herein, the following examples are set forth. It will be understood that these examples are intended to describe illustrative embodiments of the invention and are not intended to limit the scope of the invention in any way.

EXAMPLES

Example 1: PBpr1 Promoter Fused to the alaAT Gene

Construction of Binary Vectors and *Agrobacterium* Mediated Transformation

Figure 1:
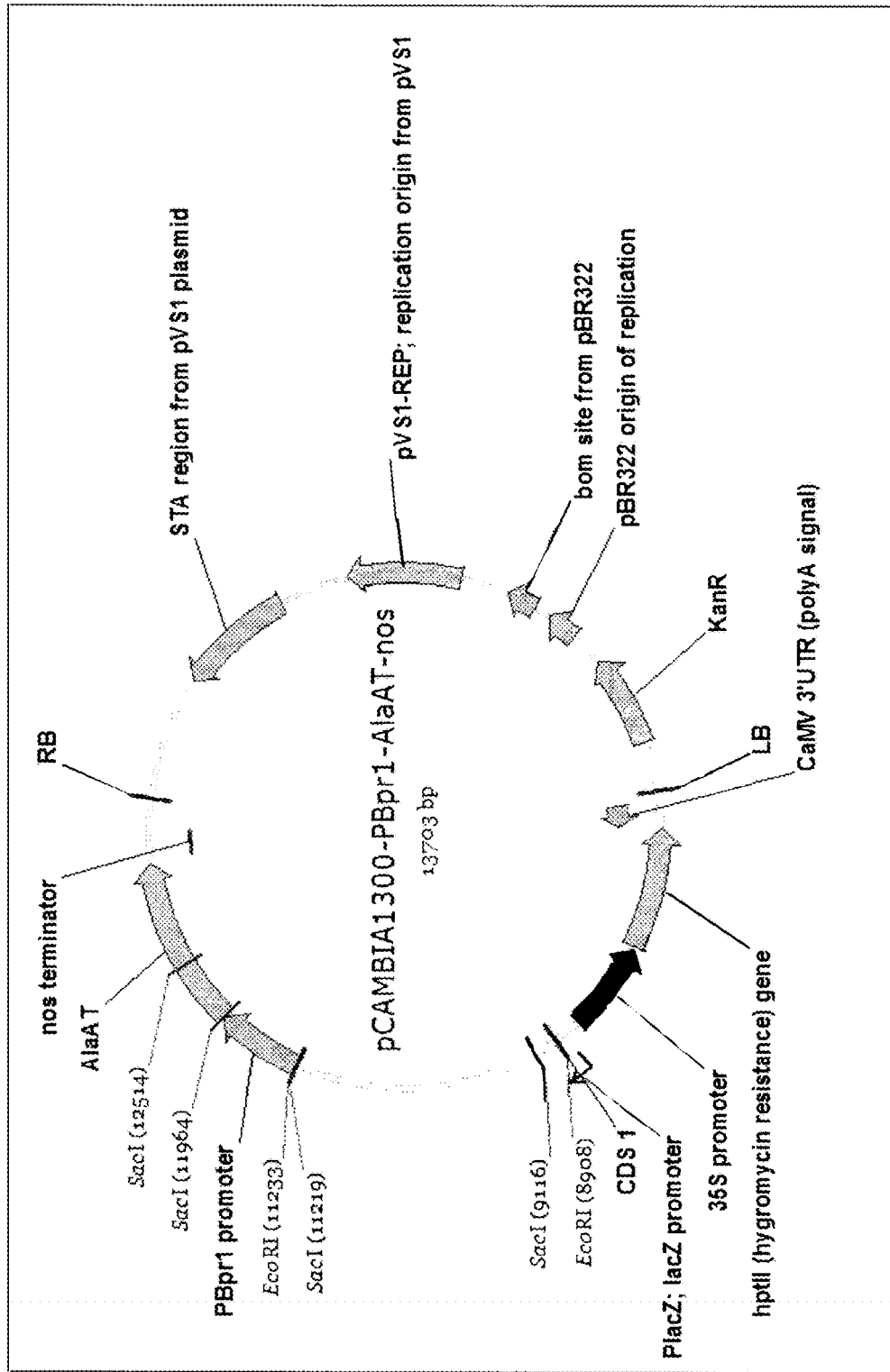
FIG. 1 shows a construct map of PBpr1::HvAlaAT in pCAMBIA1300. The HvAlaAT is driven by PBpr1 promoter and terminated by a nos terminator. The selection marker is kanamycin for plasmid selection and hygromycin.

The PBpr1 promoter was selected and designed to be cloned using GeneArt (Invitrogen, Life Technologies, Carlsbad, Calif., USA). The HvAlaATcDNA (SEQ ID NO: 2) was introduced into pCAMBIA1300 using a PstI/HindIII ligation while the PBpr1 promoter was introduced upstream of HvAlaAT to drive expression using EcoRI/SacI sites (FIGS. 1, 13). The PBpr1 promoter was introduced into pCAMBIA1305.1 to drive GUS plus for promoter pattern analysis using the EcoRI/NcoI sites. The constructs were transformed separately into *Agrobacterium tumefaciens* strain EHA105 by the freeze thaw method (Weigel and Glazebrook, 2002). Rice callus (*Oryza sativa* c.v. Nipponbare (NB)) was transformed with both constructs, using an *Agrobacterium* transformation system developed in our laboratory (Shrawat and Good, 2011). Lines transformed with PBpr1:HvAlaAT are referred to herein as PBpr1 lines while lines transformed with PBpr1::GUSplus are referred to herein as PBpr1 G lines.

Lines transformed with PBpr1:HvAlaAT were previously named Ap lines. Correspondence between the previous nomenclature and the nomenclature used herein is shown in Table 1. Likewise, lines transformed with PBpr1::GUSplus were previously named ApG lines.

Based on seed yield, total above soil biomass and tiller number at maturation, two $T_0$ lines containing PBpr1::HvAlaAT were selected to be continued through future generations. Leaf tissue was collected from two week old plants to determine if they were transgenic by means of a genomic DNA polymerase chain reaction (PCR) analysis using primers specific to the hygromycin resistant gene. Transgenic plants and null segregants to be continued to further generations were selected based on uniform size and height. Primary transgenics are designated as $T_0$ lines.

Soil Growth Chamber Experiments

To, $T_1$, and $T_2$ rice plant generations were planted in soilless-potting mixture Sunshine Mix #4 (Sun Gro Horticulture) in growth chambers at 28° C., 70% relative humidity, 14 h/10 h light/dark photoperiod, photon flux density 750 µE at bench height, as described in Shrawat et al., 2008).

In the $T_3$ generation, three seeds were germinated in a 7 inch round pot and allowed to grow for two weeks. Two of the three seedlings were culled based on uniformed height and size of plants remaining in each pot. A fertilization regime similar to that of the $T_2$ generation was started on the three week old plants. All statistical comparisons carried out for these growth chamber experiments were done using a Student's t-test.

Hydroponic Growth Chamber Experiment

The hydroponic experiment was carried out in a growth chamber at 28° C., 70% humidity, 14 h/10 h light/dark photoperiod, photon flux density 750 µE at bench height, as described by Shrawat et al., 2008. Plant material was harvested on 28 and 52 day old plants for AlaAT assays and RNA experiments.

Selection of Homozygous Lines and Maintenance of Null Lines $T_2$ seed obtained from $T_1$ plants were germinated on MS and hygromycin and the ratio of resistance to the antibiotic was measured to determine homozygosity to heterozygosity as described in Shrawat et al., 2008. Null lines were identified by PCR at the $T_1$ plant stage using hygromycin specific primers. Subsequently, null lines were selected and maintained for a comparison between NB, AGR1/7 and PBpr1 lines.

AlaAT Extraction and Enzyme Assays

Both shoot and root tissue was harvested for AlaAT enzyme assays in the hydroponic experiments, while only shoot tissue was harvested in potted experiments as per Muench and Good, 1994.

Protein SDS-PAGE Electrophoresis and Immunoblot Analysis

In order to validate the results of the AlaAT enzyme assays, SDS-PAGE electrophoresis and immunoblot analyses was carried out using the protocol of Muench and Good (1994).

RNA Extraction, cDNA Synthesis and Quantitative Real Time PCR

RNA extraction, cDNA synthesis and quantitative real time PCR was carried out using the protocol of Beatty et. al., 2009. Gene specific primer and probe pairs that were previously used by Beatty et al. (2009) were used to detect differences in gene expression due to over expression of HvAlaAT. NB plants were used as a negative control and 18srRNA was used as an endogenous control.

Bioinformatics Analysis of Promoter

The PBpr1 nucleotide sequence was selected based on homology to the OsANT1 promoter using NCBI's BLASTn program, and it was further investigated using the gene bioinformatic tools of NCBI Genbank and Refseq.

GUS Histochemical Staining

A total of 20 $T_1$ seeds of PBpr1::GUSplus transgenic lines, named PBpr1G lines, were sterilized and germinated in sterile liquid MS (4.4 g $L^{-1}$, pH 5.8) for staining. From each line, five seeds were selected at each sampling time for staining. Seedlings were sampled at 3 DAG and 7 to 10 DAG and stained for GUS expression.

Results:

Heterozygous $T_0$ Seed Yield and Biomass Preliminary Screens

At the $T_0$ stage, the independent PBpr1 plants had higher above ground biomass and seed yield compared to NB (Table 1). Two independent PBpr1 lines were selected based on high seed yield and biomass to continue on to the $T_1$ generation. When comparing the six lines selected with NB, they had significantly higher seed yield (p<0.001) and above ground biomass (p<0.001) compared to NB.

TABLE 1

Plant height, biomass and seed yield of $T_0$ PBpr1 plants and untransformed Nipponbare plants. SD refers to standard deviations.

| Lines | Previous name of line | Plant height (cm) | Total above ground biomass (g) | % Change from NB total above ground biomass | Seed yield (g) | % change from NB seed yield | Total above ground biomass without seeds (g) |
|---|---|---|---|---|---|---|---|
| PBpr1-3 | Ap10 | 86.5 | 11.6 | 6 | 3.13 | −20 | 8.47 |
| PBpr1-5 | Ap12 | 69.2 | 12.5 | 15 | 3.34 | −15 | 9.16 |
| PBpr1-7 | Ap14 | 80.8 | 13.2 | 21 | 3.37 | −14 | 9.83 |
| PBpr1-8 | Ap15 | 79.2 | 14.2 | 30 | 4.27 | 9 | 9.93 |
| PBpr1-9 | Ap16 | 74.0 | 12.4 | 14 | 4.04 | 3 | 8.36 |
| PBpr1-10 | Ap17 | 73.8 | 17.9 | 64 | 7.33 | 87 | 10.57 |
| PBpr1-11 | Ap18 | 84.3 | 17.7 | 62 | 10.01 | 156 | 7.69 |
| PBpr1-12 | Ap19 | 87.2 | 20.3 | 86 | 8.31 | 113 | 11.99 |
| PBpr1-13 | Ap20 | 85.0 | 17.8 | 63 | 7.01 | 79 | 10.79 |
| PBpr1-14 | Ap21 | 78.5 | 12.2 | 12 | 4.62 | 18 | 7.58 |
| PBpr1-15 | Ap22 | 78.0 | 12.1 | 11 | 3.49 | −11 | 8.61 |
| PBpr1-16 | Ap23 | 79.1 | 13.8 | 27 | 4.00 | 2 | 9.80 |
| PBpr1-17 | Ap24 | 86.5 | 17.2 | 58 | 6.54 | 67 | 10.66 |
| PBpr1-18 | Ap25 | 67.3 | 13.5 | 24 | 4.25 | 9 | 9.25 |
| PBpr1-19 | Ap26 | 80.2 | 15.9 | 46 | 5.51 | 41 | 10.39 |
| PBpr1-20 | Ap27 | 85.4 | 11.7 | 7 | 4.16 | 6 | 7.54 |
| PBpr1-21 | Ap28 | 86.0 | 17.4 | 60 | 7.33 | 87 | 10.07 |
| PBpr1-22 | Ap29 | 76.0 | 21.4 | 96 | 7.50 | 92 | 13.9 |
| average | | 78.0 | 14.1 | 39 | 5.45 | 40 | 9.70 |
| SD | | 6.8 | 3.63 | | 2.05 | | 1.62 |
| Nipponbare | | 75.2 | 10.9 | | 3.91 | | 7.03 |
| SD | | 6.3 | 2.17 | | 1.63 | | 1.25 |

Heterozygous $T_1$ PBpr1 Seed Yield and Biomass Preliminary Screens

Figure 2:
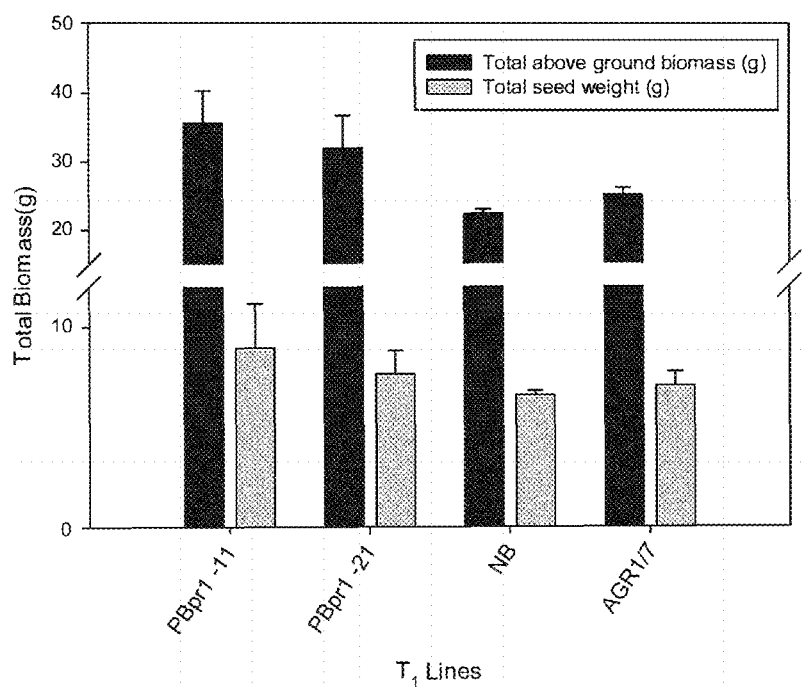
FIG. 2 shows a comparison of total above ground biomass (g) and seed yield (g) of $T_1$ PBpr1 lines, NB and AGR1/7 at maturity. Each measurement is from 5 to 7 replications and error bars are standard deviations. Black bars: Total above ground biomass (g); Grey bars: Total seed yield (g).

For further phenotypic analysis and to obtain homozygous seed, $T_1$ plants of PBpr1-11 and PBpr1-21 were grown to maturity and biomass and seed yield data collected. PBpr1-11 and PBpr1-21 had significantly higher above ground biomass than NB (p<0.05) and AGR1/7 (p<0.001) (FIG. 2). In terms of seed production, PBpr1-1 land PBpr1-21 had significantly higher seed yield than NB (p<0.05).

Figure 4:
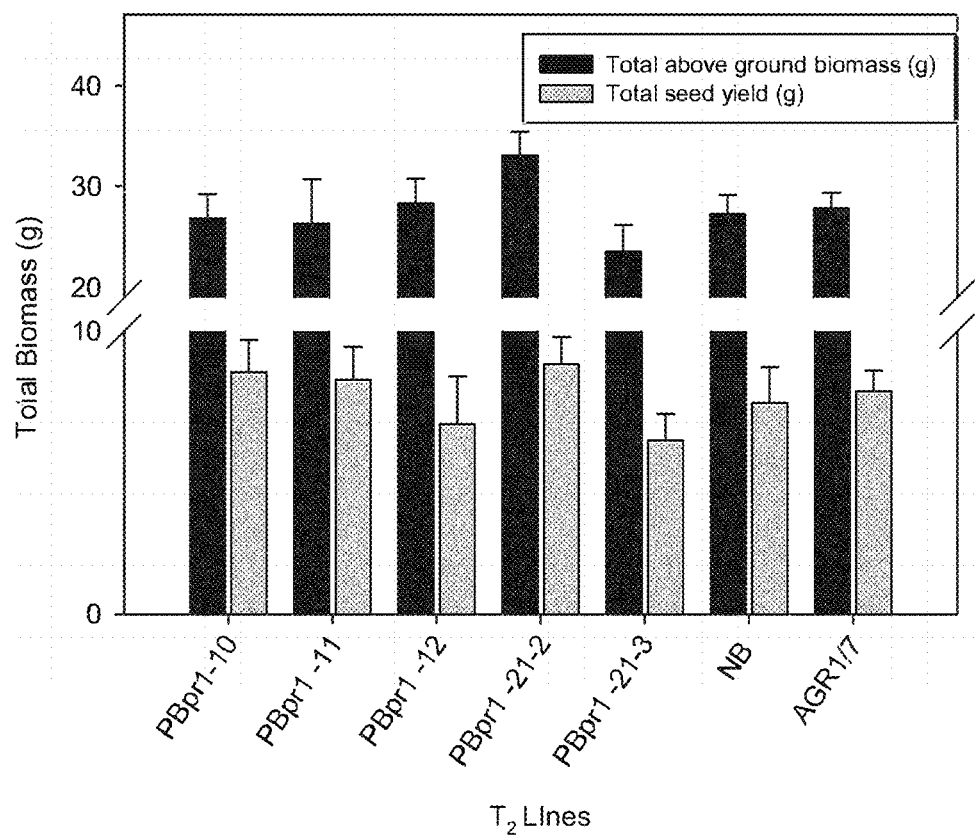
FIG. 4 shows a comparison between $T_2$ PBpr1 plants, NB and AGR1/7 above ground biomass (g) and seed yield (g) at maturity. Values from each line are from 7 replications and error bars represents SD. Black bars: Total above ground biomass (g); Grey bars: Total seed yield (g).

Growth Chamber Biomass and Seed Yield Analysis of Homozygous Lines $T_2$ homozygous PBpr1 lines were grown in soil conditions to maturity and total above ground biomass and seed yield data was collected (FIG. 4). Two of the five PBpr1 lines had higher above ground biomass than NB. Only one of these lines, PBpr1-21, was significantly larger than NB and AGR1/7 in terms of biomass (p<0.001). PBpr1-10 and PBpr1-11 were shown to have higher seed yield than NB and AGR 1/7, but these differences were not significant (p>0.05).

$T_3$ Above Ground Biomass of Homozygous PBpr1 Lines

Homozygous PBpr1 $T_3$ plants were harvested at 52 DAG in order to assess the changes of biomass at a different developmental stage (FIG. 5). PBpr1-11 and PBpr1-21, had higher dry above ground biomass than NB and the nulls at 52 DAG. PBpr1-21 had significantly higher above ground biomass than both NB and nulls (p<0.03). PBpr1-11-2N plants had similar above ground biomass compared to NB, which was consistent with previous experiments in the $T_1$ and $T_2$ generations. PBpr1-11, on the other hand, had higher biomass than NB and nulls.

PBpr1 Biomass, Seed Yield and NUE

PBpr1-21, over all 3 generations, has significantly higher above ground biomass than NB. In the $T_1$ and $T_2$ generation, PBpr1-21 is higher in above ground biomass than AGR1/7 but not significantly (FIGS. 2 and 4). PBpr1-11 also exhibits a consistent trend of higher above ground biomass than NB in the $T_1$ and $T_3$ generation but not in the $T_2$ generation (FIGS. 2, 4 and 5). Across all generations, PBpr1-21 had higher seed yield than NB and AGR1/7 while PBpr1-11 had higher seed yield than NB in the $T_1$ but not in the $T_2$ generation.

$T_1$ PBpr1 Lines Tiller Productivity

Figure 3:
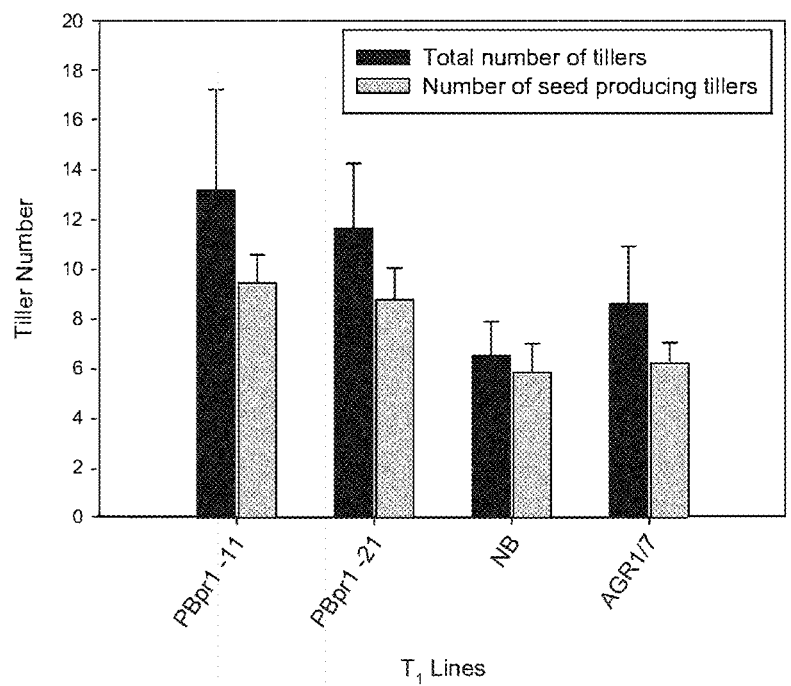
FIG. 3 shows the number of tillers and productive tillers produced by $T_1$ PBpr1 plants compared to NB and AGR1/7 at maturation. Each measurement refers to an average of at least 4 replications and error bars show SD. Black bars: Total number of tillers; Grey bars: Number of seed producing tillers.

In addition to measuring biomass and seed yield at maturity, the number of productive and non-productive tillers was measured. Tiller productivity and plant height was only recorded in soil grown plants. Tiller productivity of the PBpr1 lines, in comparison with AGR1/7 and NB was determined and all PBpr1 lines had more tillers and more productive tillers than NB (FIG. 3). PBpr1-11 and PBpr1-21 had significantly (p<0.01) more tillers and more productive tillers than AGR1/7. PBpr1-11 had the highest total number of tillers and productive tillers among all PBpr1 lines, AGR1/7 and NB. This was consistent with other parameters assessing overall plant size as PBpr1-11 produced the largest plants among all other PBpr1 lines. In comparison to AGR1/7, PBpr1-11 and PBpr1-21 had significantly more productive tillers (p<0.05).

Figure 6:
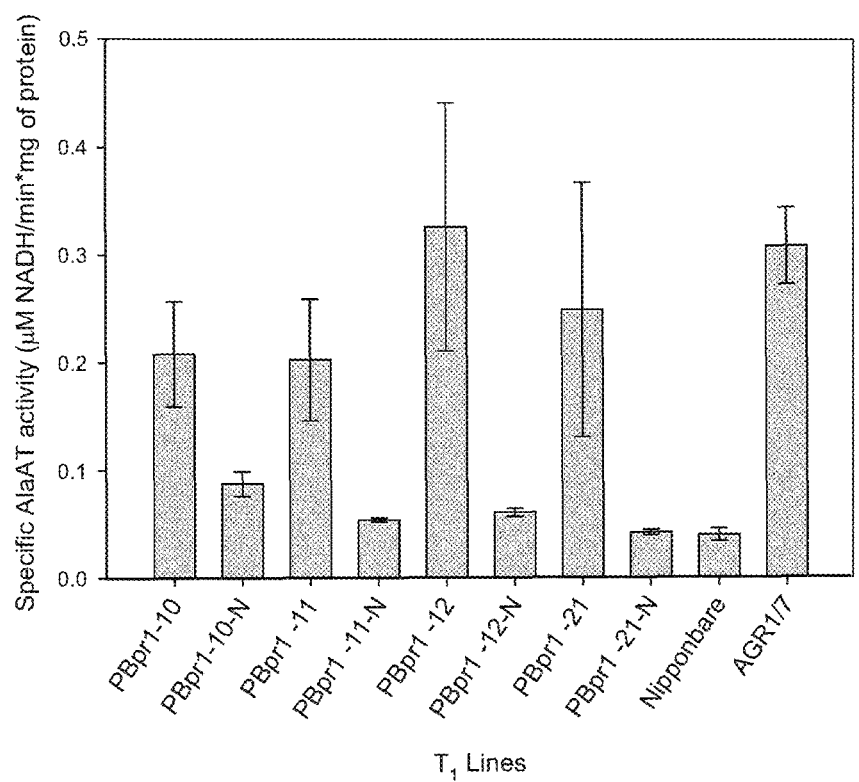
FIG. 6 shows shoot specific AlaAT activity in μM NADH/min·mg of protein of $T_1$ PBpr1 lines grown in soil at 40 days after germination (DAG) compared to NB and AGR1/7. All lines labeled with N are null segregants. Each data point for the transgenic plants was taken from an average of 3 replications and error bars refer to SD of the 3 replicates.

$T_1$ Screens for AlaAT Activity for HvAlaAT Over-Expression in Soil Grown Plants Shoots of $T_1$ soil grown PBpr1 plants were harvested between active tillering and maximum tillering stage (40 DAG) to determine their specific AlaAT activity. The different PBpr1 lines had 2.5 to 8 times higher shoot AlaAT activity compared to the null segregants and NB (FIG. 6). AlaAT specific activity was highest in PBpr1-12 and PBpr1-21 at between 3.3 to 4.3 μmoles NADH min$^{-1}$ mg of protein. AGR1/7 containing OsANT1::HvAlaAT had higher specific AlaAT activity than nulls and NB in agreement with Shrawat et al. (2008). Out of all the PBpr1 lines, only PBpr1-12 had higher average specific AlaAT activity than AGR1/7, but PBpr1-11 and PBpr1-21 had comparable levels of AlaAT activity as AGR1/7. The AGR1/7 used was a $T_5$ homozygous line while the $T_1$ PBpr1 lines tested were still segregating. Null segregants of the different PBpr1 lines (PBpr1-10-N, PBpr1-11-N, PBpr1-12-N and PBpr1-21-N) had similar AlaAT activity as NB. Once these lines were confirmed as true nulls, they were used as negative controls.

$T_3$ Homozygous Shoot AlaAT Activity Assay from Soil Grown Plants

Figure 7:
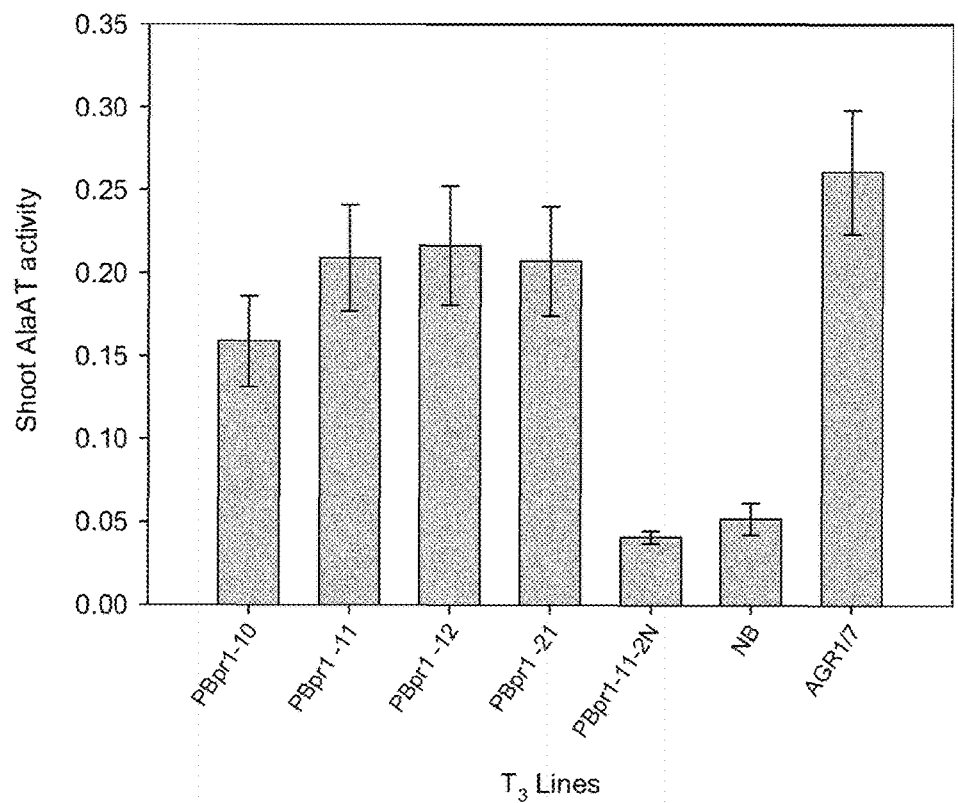
FIG. 7 shows alanine aminotransferase activity (μM NADH/min*mg of protein) of WT (NB), AGR 1/7 (OsANT1:AlaAT) and three independent PBpr1:AlaAT overexpressing $T_3$ rice lines (PBpr1-11, PBpr1-12, PBpr1-21) at five (5) different growth points during soil growth under high N conditions. Error bars refer to SD.

Independent plants of the $T_3$ generation from the lines PBpr1-10, PBpr1-11, PBpr1-12 and PBpr1-21 were identified as homozygous plants and were raised in the growth chamber until 52 DAG when tissue samples were harvested for AlaAT activity. Trends observed in the $T_3$ generation were consistent with those of the $T_1$ plants (FIG. 7). PBpr1 lines had up to 5.3 times higher shoot AlaAT activity than NB and the nulls. In agreement with $T_1$ studies in soil, PBpr1-12 had the highest AlaAT activity followed by PBpr1-11 and PBpr1-21 while PBpr1-10 had the lowest AlaAT activity.

$T_2$ Homozygous AlaAT Activity from Hydroponic Grown Plants

To assess the AlaAT activity of roots, homozygous PBpr1 lines were selected to be grown hydroponically. PBpr1 roots and shoot tissue were harvested at the beginning of active tillering (28 DAG) and at maximum tillering (52 DAG).

Shoot AlaAT Activity

Figure 8:
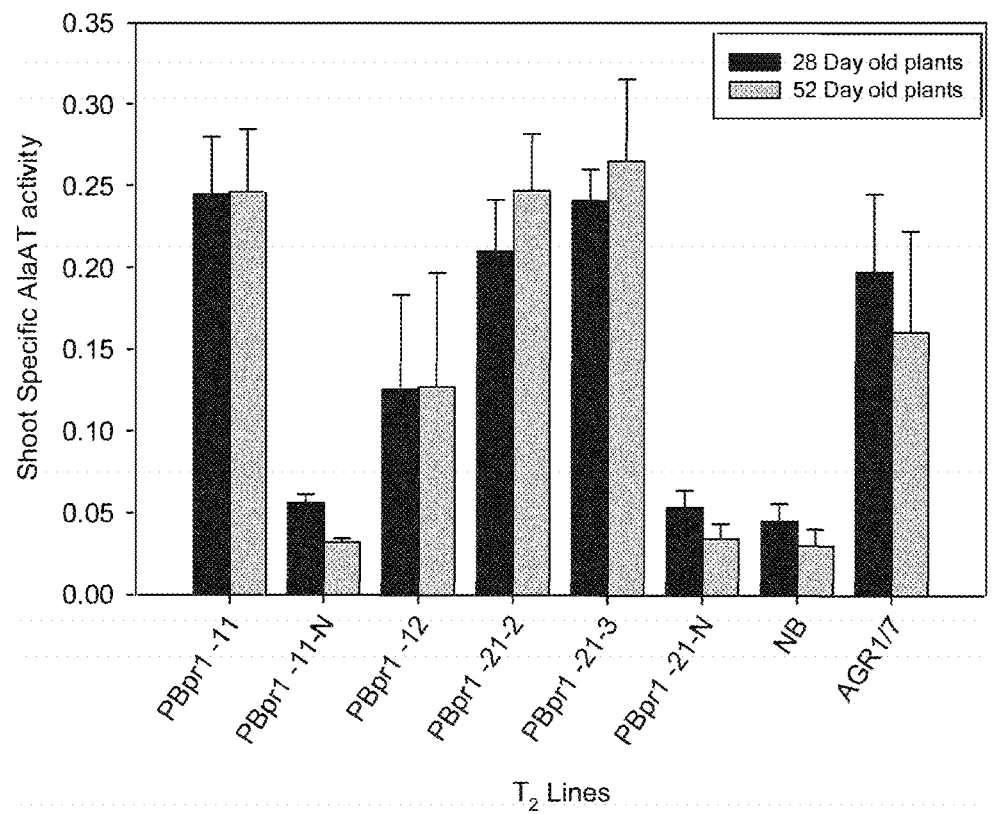
FIG. 8 shows $T_2$ PBpr1 lines shoot AlaAT activity in μM NADH/min·mg of protein at 28 and 52 days old plant that were grown hydroponically. PBpr1-21-2 and PBpr1-21-3 are siblings of the same line. Each data point referred to 5 replications and error bars refer to their SD.

The PBpr1 lines exhibit up to 8 times higher shoot AlaAT activity compared to nulls and NB (FIG. 8). At both 28 DAG and 52 DAG, PBpr1-11 and PBpr1-21 had up to 1.2 and 1.7 times higher AlaAT activity than AGR1/7 respectively. Shoot AlaAT activity of PBpr1-11 and PBpr1-21 was higher at 52 DAG than 28 DAG, whereas native shoot AlaAT activity (the PBpr1 null lines and NB) was observed to drop slightly between 28 and 52 DAG.

Between 28 DAG and 52 DAG, AlaAT activities in some of the transgenic, nulls and NB shoots were observed to have decreased with the exception of PBpr1-21. For all PBpr1 lines, the changes in shoot AlaAT activity was only between 1.1 to 1.2 times between 28 and 52 DAG.

Root AlaAT Activity

Figure 9:
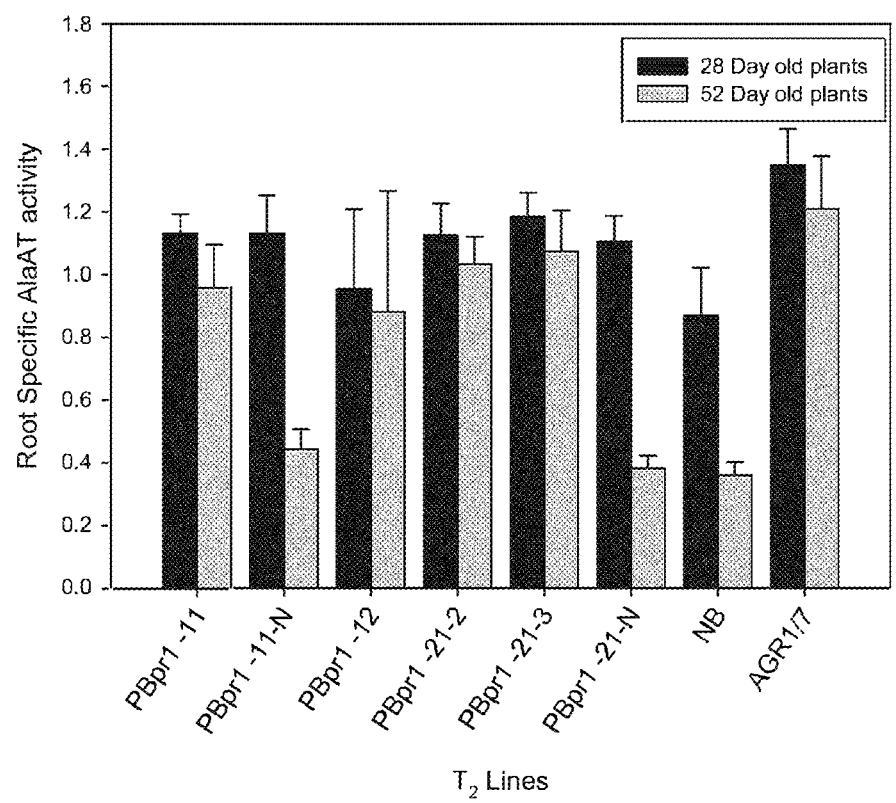
FIG. 9 shows $T_2$ PBpr1 lines root AlaAT activity at 28 and 52 days old plant grown hydroponically. Each data point referred to at least 5 replications and error bars refer to their SD. PBpr1-21-2 and PBpr1-21-3 are siblings of the same line. Black bars: 28 day old plants; grey bars: 52 day old plants.

Although all PBpr1 lines had higher root AlaAT activity than NB, similar levels of root AlaAT activity were observed between PBpr1 lines and their corresponding null siblings (FIG. 9). AGR1/7 was the only transgenic line that had clearly higher level of root AlaAT activity than all other lines. However, root AlaAT activity was observed to have dropped in all cases at 52 DAG compared to 28 DAG. The decrease was evident in null segregants and NB where levels of root AlaAT activity were observed to have dropped 2 to 3 times. A smaller decrease of 1.2 to 1.4 times in root AlaAT activity of 28 to 52 DAG was observed in the PBpr1 lines and AGR1/7. With the decrease of root AlaAT activity at 52 DAG, PBpr1 lines and AGR1/7 had up to 3 times higher AlaAT activity than NB and nulls. Shoot AlaAT activities in the non-transgenics are always low at both 28 and 52 DAG (FIG. 8). Root AlaAT activity, on the other hand, is high at 28 DAG and decreases drastically at 52 DAG. Overall root AlaAT activity in the non-transgenics was always higher than shoot AlaAT activity.

HvAlaAT Immunoblotting to Validate AlaAT Assays

Figure 10:
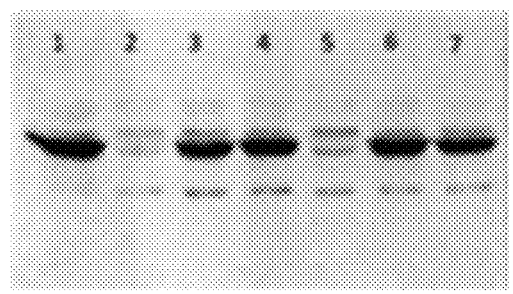
FIG. 10 shows an immunoblot analysis of protein extracts of 52 Day old $T_3$ PBpr1 lines detected with HvAlaAT-2 specific to antibody serum. Lane 1: AGR1/7, lane 2: wild-type Nipponbare, lane 3: PBpr1-10, lane 4: PBpr1-11, lane 5: PBpr1-11-2N, lane 6: PBpr1-12 and lane 7: PBpr1-21. Protein concentration was standardized across all lanes by using the Bradford protein quantifaction assay.

Fifty two day old soil grown $T_3$ PBpr1 lines were harvested to determine the stability of the PBpr1 promoter in over-expressing HvAlaAT, by AlaAT activity assays and immunoblots. $T_3$ shoots of all the PBpr1 lines tested had high levels of AlaAT protein according to the immunoblot (FIG. 10). In addition, HvAlaAT protein levels in AGR1/7 were found to be comparable but slightly higher than that of the PBpr1 lines. This was consistent with the results obtained in the AlaAT assays (FIG. 7). The 52 kDa HvAlaAT band is absent in the nulls and NB indicating the absence of HvAlaAT protein.

Figure 11:
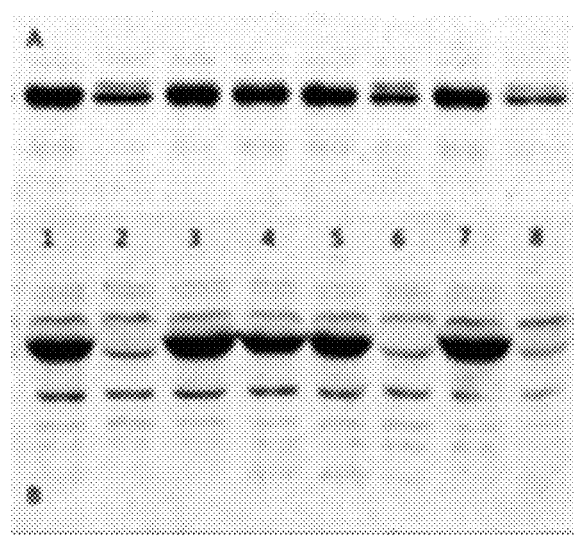
FIG. 11 shows an immunoblot analysis of protein extract from $T_2$ hydroponically grown roots (A) and shoots (B) of 28 DAG rice lines with Hv AlaAT 1° antibody detection to show amounts of HvAlaAT protein in each sample. Lane 1: PBpr1-11, lane 2: PBpr1-11-2N, lane 3: PBpr1-21-2, lane 4: PBpr1-21-3, lane 5: PBpr1-21-3 replicate, lane 6: PBpr1-21-N, lane 7: AGR1/7 and lane 8: wild-type Nipponbare. Protein concentration was standardized across all lanes by using the Bradford protein quantifaction assay.

Roots of hydroponically grown $T_2$ plants were harvested at 28 days (FIG. 11). In lines that did not carry the HvAlaAT transgene insertion, the HvAlaAT antibody bound to native AlaAT. PBpr1 and AGR1/7 roots produced a thicker and more intense band that masked the two nonspecific thinner bands representing native AlaAT at the 52 kDa region (FIG. 11, panel A). Therefore roots of 28 day old PBpr1 plants had higher levels of HvAlaAT protein than the nulls and NB.

Shoot HvAlaAT protein levels of hydroponically grown $T_2$ PBpr1 plants were also assessed at 28 (FIG. 11, panel B). HvAlaAT protein was observed to be high in the shoots of all PBpr1 lines. Again, AGR1/7 had the same level of banding intensity as all the PBpr1 lines indicating high levels of HvAlaAT protein compared to nulls and NB. At 28 days, protein levels of HvAlaAT appeared to be present and high in PBpr1 lines and absent in the non-transgenics.

qRT-PCR Analysis to Determine Gene Expression Changes from Over-Expression of HvAlaAT The mRNA expression levels of three target genes or nucleotide sequences (barley AlaAT (HvAlaAT), leucine rich repeat (LRR) and a glycine rich protein (GRP) were selected from a list of genes or nucleotide sequences that had been found to be differentially expressed in a microarray experiment comparing AGR1/7 to NB (Beatty et al., 2009).

Figure 12:
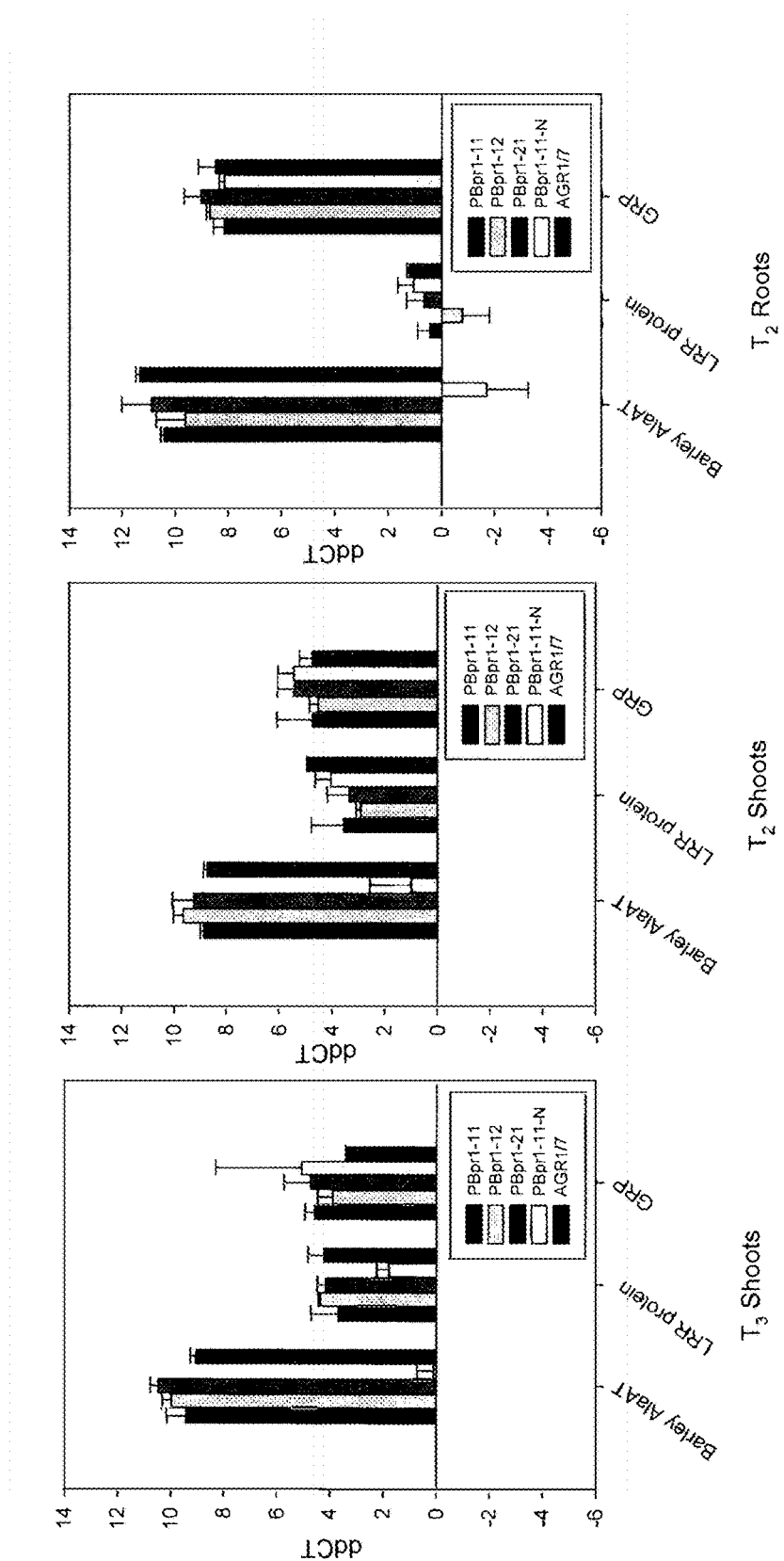
FIG. 12 shows a $Log_2$ of the relative quantification (ddCT) PBpr1 shoots, $T_2$ PBpr1 shoots and $T_2$ PBpr1 roots, AGR1/7 and null segregants of the PBpr1 lines relative to NB plants. 7 transcripts (HvAlaAT: Barley AlaAT, GRP. Glycine rich protein, LRR: Leucine rich repeat) were measured by qRT-PCR. Plants were raised in hydroponic conditions and harvested at 52 days after germination. Tissue samples used were the same with those of the AlaAT activity assays in FIG. 9. (2 fold change represents 1 ddCT. $Log_22=1$).

HvAlaAT was approximately 400 to 1400 fold higher in mRNA expression in the $T_3$, soil grown, PBpr1 lines and AGR1/7 shoots compared to NB, except for the nulls which did not differentially express HvAlaAT compared to NB (FIG. 12). The qRT-PCR analysis, AlaAT assays and immunoblotting confirmed that the PBpr1 lines were over-expressing HvAlaAT compared to the null segregant. Among the PBpr1 lines tested, PBpr1-21 had the highest HvAlaAT expression at 1400 fold higher followed by PBpr1-12 with a 1000 fold higher expression relative to NB (FIG. 12). GRP was up-regulated approximately 10 to 30 fold in all PBpr1 lines, null lines and AGR1/7. LRR was 9 to 20 fold up-regulated in the PBpr1 lines and AGR1/7 compared to NB and the nulls, which were 3.4 fold up-regulated compared to NB.

Hydronically grown $T_2$ PBpr1 shoots were analyzed using qRT-PCR to determine mRNA expression levels compared to NB. In agreement with previous AlaAT assays and immunoblots, HvAlaAT mRNA was highly expressed in all PBpr1 lines with 400 to 800 fold higher expression relative to NB with PBpr1-21 shoots having the highest up-regulation, while the null line did not differentially express HvAlaAT relative to NB (FIG. 12). All the PBpr1 lines, null line and AGR1/7 exhibited 20 to 40 fold up-regulation of GRP relative to NB. LRR was most highly up-regulated in AGR1/7 at a 29 fold change relative to NB, while the transgenic PBpr1 lines had a 7 to 11 fold up-regulation and the null line had 16 fold up-regulation.

Hydroponically grown $T_2$ PBpr1 roots RNA was analyzed for changes in transcript levels in comparison to AGR1/7 and NB. HvAlaAT mRNA was highly expressed in PBpr1 lines at an approximately 700 to 2000 fold increase compared to NB. AGR1/7 roots had 2500 fold higher expression of HvAlaAT relative to NB (FIG. 12). As expected, the null line did not show differential expression of HvAlaAT relative to NB. GRP was highly up-regulated at 200 to 500 fold in the PBpr1 lines, null line and AGR1/7 relative to NB.

GRP was more highly upregulated in roots than in shoots relative to NB in both the PBpr1 lines and AGR1/7. Similarly HvAlaAT mRNA was also more highly expressed in roots than in shoots of all the transgenic lines relative to NB (FIG. 12).

GUS Histochemical Staining of PBpr1G Plants

Three and 7 to 10 day old PBpr1G plants were stained for GUS expression to determine the expression pattern of the PB pr 1 promoter at the seedling stage (FIG. 15). GUS stains appeared at the tip of the newly emerged shoots in 3 day old plants. In 7 to 10 day old PBpr1 G plants, staining was observed in the interface between the shoots and the roots, within the remnant seed coat. Faint GUS staining was also found in the veins of the leaf blades and tillers as well as exterior of the tiller of PBpr1G plants, which may be endogenous GUS stain. With the OsANT1::GUSplus lines used as a positive control, GUS staining appeared within one hour of incubation in GUS staining buffer and GUS stains appeared in the root hairs, root tips and veins of the leaves.

PBpr1 Over-Expresses HvAlaAT.

This conclusion is supported by the following observations: high levels of AlaAT activity were observed in all the PBpr1 lines consistently throughout all generations analyzed; and immunodetection showed that there is a high level of HvAlaAT protein in transgenic plants and finally, qPCR analysis demonstrated an increase in HvAlaAT mRNA in the PBpr1 lines.

Expression from PBpr1 Promoter

At the transcript level, the OsANT1 and PBpr1 promoters both drive high level of HvAlaAT gene expression in roots and shoots compared to Nipponbare (NB) but OsANT1 drives higher levels of HvAlaAT gene expression in the roots than PBpr1 while PBpr1 drives higher levels of HvAlaAT gene expression in shoots than OsANT1 (FIG. 12).

Pattern analysis of PBpr1::GUSplus lines (PBpr1G lines) showed endogenous GUS staining in 3 day old and 7 to 10 day old seedlings while intense GUS staining was observed in the OsANT1::GUSplus line. PBpr1 may not show GUS expression but yet it drives high levels of HvAlaAT expression. This agrees with the fact that PBpr1 may be developmentally regulated in roots until after active tillering while OsANT1 drives high levels of expression at all times in both roots and shoots.

Transgenic HvAlaAT

At the protein level, PBpr1::HvAlaAT lines (PBpr1 lines) and OsANT1::HvAlaAT lines (AGR1/7) demonstrated higher levels of HvAlaAT protein in both roots and shoots from active to maximum tillering compared to NB (FIGS. 10 and 11).

At the enzymatic level, AlaAT activity of AGR1/7 was higher than NB at both active and maximum tillering in both roots and shoots. The PBpr1 lines exhibit similarly high levels of shoot AlaAT activity from active to maximum tillering compared to NB while root AlaAT activity of PBpr1 lines in roots was only observed to be higher than NB after active tillering and hence its activity seemed to be developmentally regulated in roots instead of constitutively regulated as seen in roots of AGR1/7. In shoots, AlaAT activity appears to be high at all times using the PBpr1 promoter.

HvAlaAT Over-Expressing Plant Lines

Morphologically, the PBpr1 lines produced higher seed yield and biomass compared to NB and AGR1/7 in the $T_1$, $T_2$ and $T_3$ generations. In addition, the PBpr1 lines exhibit increased tillering compared to NB and AGR1/7.

With the OsANT1 promoter, an increase in gene expression resulted in higher levels of HvAlaAT protein and consequently higher levels of AlaAT activity in both the roots and shoots of AGR1/7. In contrast, although the PBpr1 promoter drove high levels of HvAlaAT expression and HvAlaAT protein levels, this did not result in an increase in AlaAT activity until after active tillering in roots. In shoots, an increase in HvAlaAT gene expression driven by PBpr1 promoter resulted in both increased protein levels and AlaAT activity. This suggests that PBpr1 may be developmentally regulated in rice roots.

The nitrogen use efficiency (NUE) of three independent PBpr1 lines, AGR1/7 and NB were calculated from the seed yield per gram of nitrogen applied per plant (Table 2). The three PBpr1 lines were all higher in NUE than AGR 1/7 by 5-12% and NB by 11-18%. The highest NUE line was PBpr1-21 and the lowest was NB.

Table 3 shows yield tests and agronomic traits from three PBpr1:AlaAT over-expressing rice lines (PBpr1-11, PBpr1-12, PBpr1-21 (OsPBpr1::HvAlaAT).) versus WT (NB; Nipponbare) at maturity during soil growth under high N conditions.

FIG. 15 shows the foliar amino acid concentrations of wildtype (cv. Nipponbare) rice versus barley AlaATover-expressing rice transgenic rice lines; AGR 1/7 (OsANT1:HvAlaAT) and PBpr1-11, PBpr1-12, PBpr1-21 (OsPBpr1::HvAlaAT).

Measurements were taken at 28, 40, 52 and 95 days after germination (DAG) corresponding to active tillering, mid-tillering, maximum tillering and flag leaf emergence, respectively. Amino acid concentration (nM/g FW) are averages of 4 replicates.

TABLE 2

NUE of $T_2$ homozygous PBpr1 lines, AGR1/7 and Nipponbare (NB) plants (based on seed yield per gram of nitrogen applied per plant and the above ground biomass without seed. Each data point is taken from at least 4 replicates.

|  | Above ground biomass without seed (g) | Seed yield (g) | NUE (yield · unit applied$^{-1}$) |
|---|---|---|---|
| PBpr1-10 | 18.26 | 8.55 | 43.63 |
| PBpr1-11 | 18.03 | 8.29 | 42.27 |
| PBpr1-21 | 24.20 | 8.83 | 45.07 |
| NB | 19.75 | 7.48 | 38.16 |
| AGR1/7 | 19.94 | 7.89 | 40.23 |

(NUE = Grain yield/N applied))

Example 2: PBpr2 Promoter Fused to the alaAT Gene

TABLE 3

Yield tests and agronomic traits from three PBpr1: AlaAT over-expressing rice lines versus WT.

| Trait | NB | PBpr1-11 | PBpr1-12 | PBpr1-21 |
|---|---|---|---|---|
| Average days to flowering | 92-105 | 88-99 | 93-100 | 94-110 |
| Producing tillers | 6.5 | 6.6 | 6.4 | 7.2 |
| Nonproducing tillers | 0.25 | 0.6 | 0.2 | 0.4 |
| Seed weight | 10.3 ± 0.5 | 9.9 ± 0.5 | 8.5 ± 0.2 | 9.7 ± 0.5 |
| Fresh weight biomass per plant (g) | 24.9 ± 1.4 | 26.9 ± 2.0 | 25.5 ± 1.9 | 25.7 ± 2.7 |

TABLE 3-continued

Yield tests and agronomic traits from three PBpr1: AlaAT over-expressing rice lines versus WT.

| Trait | NB | PBpr1-11 | PBpr1-12 | PBpr1-21 |
|---|---|---|---|---|
| Dry weight per plant (g) | 14.6 ± 0.9 | 17.4 ± 1.5 | 17.5 ± 1.3 | 16.7 ± 2.0 |
| % dry weight of NB | | 108% | 102% | 103% |

The choice of promoter to use to drive expression of a gene, such as the alanine aminotransferase gene, in crop plants is important for optimal expression of the gene at the right time (developmental stage) and the right place in the plant (tissue specificity). The promoter chosen to drive the expression will affect the phenotypic outcome for the plant. There are examples in the literature where the promoter chosen to drive a gene of interest affects the phenotypic outcome. For example, Myashita et al., (2007) used the CaMV35S promoter to drive expression of AlaAT in Arabidopsis and observed no phenotype. Furtado et al., (2008) studied the ability of various promoters to drive expression of green fluorescent protein (GFP) in transgenic rice and showed that three out of five putative endosperm specific promoters from rice, barley and wheat did not allow GFP expression in glumes/lemma/palea of the flower tissues, while the other two did allow GFP expression in those plant parts. The choice of promoter to use therefore requires both careful design and experiments to determine its efficacy to improve NUE.

Prior to the studies outlined in Example 1, a promoter named "PBpr2" was selected because its native gene is homologous to rice aldehyde dehydrogenases, such as the OsANT1 gene. The sequence of the PBpr2 promoter is provided in SEQ ID NO: 4. Based on sequence similarity the PBpr2 gene is a putative aldehyde dehydrogenase, however, its function is unknown.

An alignment of the sequences of the PBpr1, PBpr2 and OsANT1 promoters (SEQ ID NOs: 1, 4 and 5, respectively) is shown in FIG. 17. Although neither the Softberry nor the PlantpromoterDB software predicted a TATA box in PBpr1 at the same location as is present for OsANT1 or PBpr2, there is a conserved TATGAG sequence at that location. Also, PBpr1 includes a regulatory element about 30 nt downstream of the TATA boxes, and although the promoter prediction software does not predict a regulatory element at the corresponding position for the other two promoters, it is in a section of DNA with high conservation between the three sequences. The sequence identity between the PBpr1 and PBpr2 sequences, based on the alignment shown in FIG. 17, is approximately 50% over the entire length (733 nucleotides) of the PBpr1 sequence.

The PBpr2 promoter was fused to the alaAT gene and a Nos terminator sequence and used to drive expression of AlaAT in rice following protocols similar to those outlined in Example 1. The results of these experiments are shown in FIG. 16 and show that PBpr2 does not increase plant height, above ground biomass or seed yield compared to control wild-type (Nipponbare) rice, and so does not promote an NUE phenotype.

Collectively, the results from Examples 1 and 2 show that despite their similarities, including an approximately 50% sequence identity, the PBpr1 and PBpr2 promoters when fused to the AlaAT gene have different effects on phenotypic outcome.

The disclosures of all patents, patent applications, publications and database entries referenced in this specification are hereby specifically incorporated by reference in their entirety to the same extent as if each such individual patent, patent application, publication and database entry were specifically and individually indicated to be incorporated by reference.

Although the invention has been described with reference to certain specific embodiments, various modifications thereof will be apparent to those skilled in the art without departing from the spirit and scope of the invention. All such modifications as would be apparent to one skilled in the art are intended to be included within the scope of the following claims.

REFERENCES

Beatty, P. H., Shrawat, A. K., Carroll, R. T., Zhu, T., and Good, A. G. (2009) *Plant Biotechnology Journal* 7, 562-576

Burton, R. A., et al. (2011). *Plant Biotechnology Journal* 9, 117-135.

Freeman, J., Sparks, C. A, West, J., Shewry, P. R., and Jones, H. D. (2011). *Plant biotechnology journal* 9 (7): 788-796.

Furtado, A., Henry, R. J., and Takaiwa, F. (2008) *Plant Biotechnology Journal* 6, 679-693.

Gao, C., and Han, B. (2009). *Gene* 431, 86-94.

Good A. G. and Beatty P. H. (2011b) Biotechnological Approaches to Improving Nitrogen Use Efficiency in Plants: Alanine Aminotransferase as a Case Study. In, *The Molecular and Physiological Basis of Nutrient Use Efficiency in Crops*, First Edition. Edited by Malcolm J. Hawkesford, Peter Barraclough. John Wiley & Sons, Inc. Published 2011 by John Wiley & Sons, Inc.

Good, A. G., Johnson, S. J., DePauw, M. D., Carroll, R. T., Savidov, N., Vidamir, J., Lu, Z., Taylor, G. and Stroeher, V. (2007) *Canadian Journal of Botany* 85, 252-262.

Kasuga, M., Liu, Q., Miura, S., Yamaguchi-Shinozaki, K., and Shinozaki, K. (1999). *Nature Biotechnology* 17, 287-291

Ma et al., 2009, *Plant Cell Rep.* 28 (11):1759-65. Epub 2009 Oct. 10.

Muench, D. G., and Good, A. G. (1994) *Plant Molecular Biology* 24, 417-427.

Oguchi, K., Tanaka, N., Komatsu, S., and Akao, S. (2004) *Plant cell reports* 22, 848-858.

Park, T. H., and Jones, J. D. G. (2008) *Euphytica* 166, 331-339.

Pino et al., 2007 *Plant Biotechnol J.* 5 (5):591-604. Epub 2007 Jun. 8.

Qu, L. Q., and Takaiwa, F. (2004) *Plant Biotechnology Journal* 2, 113-125.

Shelton, A. M., Zhao, J., and Roush, R. T. (2002). *Annual Reviews in Entomology* 47, 845-881

Shrawat, A. K., and Good, A. G. (2011). *Methods in molecular biology* 710, 355-372.

Shrawat, A. K., Carroll, R. T., DePauw, M., Taylor, G. J. and Good, A. G. (2008) *Plant Biotechnology Journal* 6, 722-732.

Sweetlove, L. J., Heazlewood, J. L., Herald, V., Holtzapffel, R., Day, D. A., Millar, A. H. (2002) *Plant Journal* 32, 891-904

Tanaka, N., Takahashi, H., Kitano, H., Matsuoka, M., Akao, S., Uchimiya, H., and Komatsu, S. (2005). *Journal of proteome research* 4 (5), 1575-1582.

Weber, D. (2003). *Pesticide Outlook* 14, 256-259.

Weigel, D., and Glazebrook, J. (2002) *Arabidopsis*: A Laboratory Manual. Cold Spring Harbor Laboratory Press, Cold Spring Harbor, N.Y.

Wu, C. Y., Adachi, T., Hatano, T., Washida, H., Suzuki, A., and Takaiwa, F. (1998) *Plant Cell Physiology* 39, 885-889.

Xue, G-P., Way, H. M., Richardson, T., Drenth, J., Joyce, P. A., and McIntyre, C. L. (2011). *Molecular Plant* 1-16.

The invention claimed is:

1. A transgenic monocot plant, plant cell or plant part comprising a polynucleotide encoding an alanine aminotransferase comprising the amino acid sequence of SEQ ID No. 3 operably linked to a PBpr1 promoter comprising the nucleotide sequence of SEQ ID No. 1.

2. The transgenic plant, plant cell or plant part according to claim 1, wherein the plant is wheat, maize, rice, or barley.

3. The transgenic monocot plant, plant cell or plant part according to claim 1, wherein the polynucleotide encoding an alanine aminotransferase comprises the nucleotide sequence of SEQ ID No. 2.

4. A seed obtained from the transgenic monocot plant according to claim 1, the seed comprising a polynucleotide encoding an alanine aminotransferase comprising the amino acid sequence of SEQ ID No. 3 operably linked to a PBpr1 promoter comprising the nucleotide sequence of SEQ ID No. 1.

5. A genetic construct comprising a polynucleotide encoding an alanine aminotransferase comprising the amino acid sequence of SEQ ID No. 3 operably linked to a PBpr1 promoter comprising the nucleotide sequence of SEQ ID No. 1.

6. The genetic construct according to claim 5, wherein the polynucleotide encoding an alanine aminotransferase comprises the nucleotide sequence of SEQ ID No. 2.

7. A method of generating a monocot plant having increased nitrogen use efficiency, increased biomass, increased seed yield, increased tillering or a combination thereof, comprising:
transforming a monocot plant cell with the genetic construct according to claim 5, and growing the transformed monocot plant cell to produce a monocot plant that expresses the alanine aminotransferase under control of the PBpr1 promoter, wherein the monocot plant has increased nitrogen use efficiency, increased biomass increased seed yield, increased tillering or a combination thereof compared to a wild-type monocot plant grown under identical conditions.

8. A method for producing a monocot plant having increased nitrogen use efficiency, increased biomass, increased seed yield, increased tillering or a combination thereof, comprising:
growing a monocot plant from a seed or regenerating a monocot plant from a plant part, wherein the plant part or seed comprises the genetic construct according to claim 5,
wherein the monocot plant has increased nitrogen use efficiency, increased biomass, increased seed yield, increased tillering or a combination thereof compared to a wild-type monocot plant grown under identical conditions.

9. The method of claim 8, further comprising providing a fertilizer to the monocot plant or the habitat of the monocot plant.

10. The method of claim 9, wherein the fertilizer is a nitrogen containing fertilizer.

11. The method according to claim 7, wherein the plant is wheat, maize, rice, or barley.

12. A process for increasing nitrogen use efficiency, biomass, seed yield, increased tillering or a combination thereof, in a monocot plant comprising:
applying an herbicide, insecticide, fertilizer, or combination thereof, to a monocot seed comprising the genetic construct according to claim 5, and
growing a monocot plant from the seed, wherein the monocot plant has increased nitrogen use efficiency, increased biomass, increased seed yield, increased tillering or a combination thereof compared to a wild-type monocot plant grown under identical conditions.

13. The method according to claim 8, wherein the plant is wheat, maize, rice, or barley.

* * * * *

SEQUENCE LISTING

<160> NUMBER OF SEQ ID NOS: 6

<210> SEQ ID NO 1
<211> LENGTH: 733
<212> TYPE: DNA
<213> ORGANISM: artificial sequence
<220> FEATURE:
<223> OTHER INFORMATION: PBpr1 promoter

<400> SEQUENCE: 1

| | | | | | |
|---|---|---|---|---|---|
| gaattctgaa | agtttccgtc | caaatcgcac | cttttaaccg | tttgaaaaac | atacaaacga | 60 |
| aaaataatct | atatcttaat | caggaagaaa | gagtacgaaa | tggtgaaccg | tcgaaactat | 120 |
| tcatatacgt | cgtctgtctc | atgaaaaaaa | aaatcaatcc | agaaggatac | gagacacttt | 180 |
| tacttcaaca | aatatagaca | tgagcttatt | ctactaggtt | tggttgttta | ataagacgaa | 240 |
| agaaatacat | tggttagttt | ttcattaaaa | aataatcgtt | tgactgacat | aaacctagga | 300 |
| aatactggat | taagatagat | cagtaggatt | aagatccact | gatgtaattt | cccactgatt | 360 |
| tggtggctga | catgtggacc | tgagagttgt | gtgggctcac | atgtcaaatc | acggtgaaca | 420 |
| gtacgtcacg | atatgttaga | ggttcctctt | ccggagatac | ttatacgaat | tttgcggaaa | 480 |
| cctgcaaact | ttgatggacg | attgaggcga | gtttagttct | aaattttttc | ttcaaacttc | 540 |
| taacttttc | atcacatcgt | ttcaatttca | atcaaacttc | caatgttgac | gtgaactaaa | 600 |
| cacacctatg | agatatgaga | agcgggttga | cacttgacaa | gtcctgacat | gctgtgttgg | 660 |
| cgtgggcccc | acctgccacg | tcaggtccag | ctccgggtgg | ttgggtttgg | tgctttccga | 720 |
| taggcacgag | ctc | | | | | 733 |

<210> SEQ ID NO 2
<211> LENGTH: 1455
<212> TYPE: DNA
<213> ORGANISM: Hordeum vulgare

<400> SEQUENCE: 2

| | | | | | |
|---|---|---|---|---|---|
| atggctgcca | ccgtcgccgt | ggacaacctg | aaccccaagg | ttttaaaatg | tgagtatgct | 60 |
| gtgcgtggag | agattgtcat | ccatgctcag | cgcttgcagg | aacagctaaa | gactcaacca | 120 |
| gggtctctac | cttttgatga | gatcctctat | tgtaacattg | gaacccaca | atctcttggt | 180 |
| cagcaaccag | ttacattctt | cagggaggtt | cttgcccttt | gtgatcatcc | agacctgttg | 240 |
| caaagagagg | aaatcaaaac | attgttcagt | gctgattcta | tttctcgagc | aaagcagatt | 300 |
| cttgccatga | tacctggaag | agcaacagga | gcatacagcc | atagccaggg | tattaaagga | 360 |
| cttcgtgatg | caattgcttc | tgggatcgct | tcacgagatg | gattccctgc | taatgctgat | 420 |
| gacatttttc | tcacagatgg | agcaagtcct | ggggtgcacc | tgatgatgca | attactgata | 480 |
| aggaatgaga | agatggcat | tcttgtcccg | attcctcagt | accccttgta | ctcggcttcc | 540 |
| atagctcttc | atggcggagc | tcttgtccca | tactatctca | atgaatcgac | gggctggggt | 600 |
| ttggaaacct | ctgatgttaa | gaagcaactt | gaagatgctc | ggtcaagagg | catcaacgtt | 660 |
| agggcttttgg | tggttatcaa | tccaggaaat | ccaactggac | aggtacttgc | tgaagaaaac | 720 |
| caatatgaca | tagtgaagtt | ctgcaaaaat | gagggtcttg | ttcttctagc | tgatgaggta | 780 |
| taccaagaga | acatctatgt | tgacaacaag | aaattccact | ctttcaagaa | gatagtgaga | 840 |

-continued

```
tccttgggat acggcgagga ggatctccct ctagtatcat atcaatctgt ttctaaggga    900
tattatggtg agtgtggtaa aagaggtggt tactttgaga ttactggctt cagtgctcca    960
gtaagagagc agatctacaa aatagcatca gtgaacctat gctccaatat cactggccag   1020
atccttgcta gtcttgtcat gaacccacca aaggctagtg atgaatcata cgcttcatac   1080
aaggcagaaa aagatggaat cctcgcatct ttagctcgtc gtgcgaaggc attggagcat   1140
gcattcaata aacttgaggg aattacttgc aacgaggctg aaggagcaat gtacgtgttc   1200
cctcaaatct gtctgccaca gaaggcaatt gaggctgcta agctgctaa caaagcacct    1260 gatgcattct atgctcttcg tctcctcgag tcgactggaa tcgtcgttgt ccctggatca   1320
ggatttggcc aggttcctgg cacatggcac ttcaggtgca cgatccttcc gcaggaggat   1380
aagatcccgg cagtcatctc ccgcttcacg gtgttccatg aggcgttcat gtcagagtat   1440
cgtgactaaa ctggt                                                    1455
```

<210> SEQ ID NO 3
<211> LENGTH: 482
<212> TYPE: PRT
<213> ORGANISM: Hordeum vulgare

<400> SEQUENCE: 3

```
Met Ala Ala Thr Val Ala Val Asp Asn Leu Asn Pro Lys Val Leu Lys
1               5                  10                  15

Cys Glu Tyr Ala Val Arg Gly Glu Ile Val Ile His Ala Gln Arg Leu
                20                  25                  30

Gln Glu Gln Leu Lys Thr Gln Pro Gly Ser Leu Pro Phe Asp Glu Ile
            35                  40                  45

Leu Tyr Cys Asn Ile Gly Asn Pro Gln Ser Leu Gly Gln Gln Pro Val
        50                  55                  60

Thr Phe Phe Arg Glu Val Leu Ala Leu Cys Asp His Pro Asp Leu Leu
65                  70                  75                  80

Gln Arg Glu Glu Ile Lys Thr Leu Phe Ser Ala Asp Ser Ile Ser Arg
                85                  90                  95

Ala Lys Gln Ile Leu Ala Met Ile Pro Gly Arg Ala Thr Gly Ala Tyr
                100                 105                 110

Ser His Ser Gln Gly Ile Lys Gly Leu Arg Asp Ala Ile Ala Ser Gly
            115                 120                 125

Ile Ala Ser Arg Asp Gly Phe Pro Ala Asn Ala Asp Ile Phe Leu
        130                 135                 140

Thr Asp Gly Ala Ser Pro Gly Val His Leu Met Met Gln Leu Leu Ile
145                 150                 155                 160

Arg Asn Glu Lys Asp Gly Ile Leu Val Pro Ile Pro Gln Tyr Pro Leu
                165                 170                 175

Tyr Ser Ala Ser Ile Ala Leu His Gly Gly Ala Leu Val Pro Tyr Tyr
            180                 185                 190

Leu Asn Glu Ser Thr Gly Trp Gly Leu Glu Thr Ser Asp Val Lys Lys
        195                 200                 205

Gln Leu Glu Asp Ala Arg Ser Arg Gly Ile Asn Val Arg Ala Leu Val
    210                 215                 220

Val Ile Asn Pro Gly Asn Pro Thr Gly Gln Val Leu Ala Glu Glu Asn
225                 230                 235                 240

Gln Tyr Asp Ile Val Lys Phe Cys Lys Asn Glu Gly Leu Val Leu Leu
                245                 250                 255

Ala Asp Glu Val Tyr Gln Glu Asn Ile Tyr Val Asp Asn Lys Lys Phe
```

His Ser Phe Lys Lys Ile Val Arg Ser Leu Gly Tyr Gly Glu Glu Asp
    260                 265                 270
                275                 280                 285

Leu Pro Leu Val Ser Tyr Gln Ser Val Ser Lys Gly Tyr Tyr Gly Glu
290                 295                 300

Cys Gly Lys Arg Gly Tyr Phe Glu Ile Thr Gly Phe Ser Ala Pro
305                 310                 315                 320

Val Arg Glu Gln Ile Tyr Lys Ile Ala Ser Val Asn Leu Cys Ser Asn
                325                 330                 335

Ile Thr Gly Gln Ile Leu Ala Ser Leu Val Met Asn Pro Pro Lys Ala
                340                 345                 350

Ser Asp Glu Ser Tyr Ala Ser Tyr Lys Ala Glu Lys Asp Gly Ile Leu
                355                 360                 365

Ala Ser Leu Ala Arg Arg Ala Lys Ala Leu Glu His Ala Phe Asn Lys
                370                 375                 380

Leu Glu Gly Ile Thr Cys Asn Glu Ala Glu Gly Ala Met Tyr Val Phe
385                 390                 395                 400

Pro Gln Ile Cys Leu Pro Gln Lys Ala Ile Glu Ala Ala Lys Ala Ala
                405                 410                 415

Asn Lys Ala Pro Asp Ala Phe Tyr Ala Leu Arg Leu Leu Glu Ser Thr
                420                 425                 430

Gly Ile Val Val Pro Gly Ser Gly Phe Gly Gln Val Pro Gly Thr
                435                 440                 445

Trp His Phe Arg Cys Thr Ile Leu Pro Gln Glu Asp Lys Ile Pro Ala
                450                 455                 460

Val Ile Ser Arg Phe Thr Val Phe His Glu Ala Phe Met Ser Glu Tyr
465                 470                 475                 480

Arg Asp

<210> SEQ ID NO 4
<211> LENGTH: 931
<212> TYPE: DNA
<213> ORGANISM: artificial sequence
<220> FEATURE:
<223> OTHER INFORMATION: PBpr2 promoter

<400> SEQUENCE: 4
gaattcatat agtatctttg tatgttgagc attagtattc agtgagttaa aactttatag     60
ttgttagtgg atgagtttga gttttaggat ttagtggggt attataattt catggtaaga    120
taggatgagt atatataatt agggattaaa ttacaatatt ttaaggatca tatcgatatt    180
caaaacaata tgtttttta agatggatgg aatcaatttt ctgagatatg tcccgctggg    240
gtgtccacaa tctgcacgcc atatctgact acacatatac aacgcccatc ctctgtcgat    300
ctccttgtgt aaacacaacc gtccgtgaca cgtacgtaca tggggatag cttgcctctc     360 cgttcagttg cgtgacaact aataaaatac taacacaatg tcttaatcct ccaaaaaaaa    420
actcctaaat aattaattaa agataaggca agaaattaat ccaaatagtc caaaacaata    480
ggataaagag gagagcaaaa ctccaaatgg tcacacgtct ctcggtgtca ttttctcgtc    540
ggcttgcttt gtttgattcc agagtttccc aaactctcta gagagcaagt caaacagatc    600
tcatcgatcg cccaagaaga agacacatcc acaaataata atctcatctt atcgtactaa    660
tttatcttaa tacagtgtaa taaactatat cagtttgaga tattttttc ctgtctaaat    720 tatctccaaa ccgtaggaat tttcgcaccc gacgatctct tttcttgatt tttcaaacca    780

```
aacggaccaa tctctctcgc gtgtatatat agcgaggtgg agctcgagct ccatgcctgc    840
ttcctcctga ctcctctcct gcattctctc gcttctgacg gcggcaacta accttttggg    900
gattcgattc gaggaggagg tgatgggatc c                                   931

<210> SEQ ID NO 5
<211> LENGTH: 973
<212> TYPE: DNA
<213> ORGANISM: artificial sequence
<220> FEATURE:
<223> OTHER INFORMATION: OsANT1 promoter

<400> SEQUENCE: 5
aggaagtgat ttttagcgta gctgtgtttg tagcgtaatt gcgtaaagtc ctttcaattt     60
tgctatatct cactcgaaag attttttctt atctctcact cgattttctc actcaaattt    120
acagtgtatt ttcttgtaag ttacagtgta atttatgaaa cttacactgt aacttttgta    180
agttacactg taattttga atcttcacat gtaaatttta aattttgtat tggatttggt     240 cttttttcttg aggatatggt aatttaatgt tcattatggt gtttcttaat tgcttttgc    300 tttttattat atctatcgga ttttaataca aagattaaaa atctgtgtga tacgattata    360 aaaatcttc gaaagatgta taggtactcc caagccctt taagaaagtt ttcaagaca       420 aaagttttg gatgaaaggt agttataggg aaaaaggaat gtgcgtttat gtttatttgc    480
attgcttatt agcaaccaaa aactaatcta taagtaaatc ttttatatac gtgcgcttaa    540
taattcaaaa gcaaattcat gtaaaataaa atgcgatgaa gaaactttaa aaagttatca    600
aatttagatt ttattaaatt ttagttaca agagcgctac gatgaaggct ttaaaaagat     660
gggaaaataa aacctttgac ctttctggac ttcaccaaac agctcacgct ttcggcttcg    720
tgccgtctcg tcccgtgcta ctgctacccc ctcctgaccc cacccgccac tccacgctcc    780
cttctcctcc ccttcccgtg acacacagtc cccactccac cgcctccgta taagtatccc    840
ttccttaccg ccggccagcc acagccaccg cctcccccac cccacccga tcccctcccc    900 gccgtacggg cgcagaagga acccgtcttc tagaaggagg aggagggcta cctctctctc    960
tctctcttct gcc                                                       973

<210> SEQ ID NO 6
<211> LENGTH: 745
<212> TYPE: DNA
<213> ORGANISM: artificial sequence
<220> FEATURE:
<223> OTHER INFORMATION: PBpr1 promoter sequence including start codon

<400> SEQUENCE: 6
gaattctgaa agtttccgtc caaatcgcac cttttaaccg tttgaaaaac atacaaacga     60
aaaataatct atatcttaat caggaagaaa gagtacgaaa tggtgaaccg tcgaaactat    120
tcatatacgt cgtctgtctc atgaaaaaaa aaatcaatcc agaaggatac gagacacttt    180
tacttcaaca aatatagaca tgagcttatt ctactaggtt tggttgttta ataagacgaa    240
agaaatacat tggttagttt ttcattaaaa aataatcgtt tgactgacat aaacctagga    300
aatactggat taagatagat cagtaggatt aagatccact gatgtaattt cccactgatt    360
tggtggctga catgtggacc tgagagttgt gtgggctcac atgtcaaatc acggtgaaca    420
gtacgtcacg atatgttaga ggttcctctt ccggagatac ttatacgaat tttgcggaaa    480
cctgcaaact ttgatggacg attgaggcga gtttagttct aaatttttc ttcaaacttc    540 taacttttc atcacatcgt ttcaatttca atcaaacttc caatgttgac gtgaactaaa    600
```

```
cacacctatg agatatgaga agcgggttga cacttgacaa gtcctgacat gctgtgttgg    660
cgtgggcccc acctgccacg tcaggtccag ctccgggtgg ttgggtttgg tgctttccga    720
taggcacgag ctcatggctg ccacc                                          745
```